US011839213B2

(12) United States Patent
Neas et al.

(10) Patent No.: US 11,839,213 B2
(45) Date of Patent: Dec. 12, 2023

(54) ANTIMICROBIAL, DISINFECTING, AND WOUND HEALING COMPOSITIONS AND METHODS FOR PRODUCING AND USING THE SAME

(71) Applicant: Armis Biopharma, Inc., Fort Collins, CO (US)

(72) Inventors: Edwin Neas, Nunn, CO (US); Scott Noblitt, Fort Collins, CO (US)

(73) Assignee: ARMIS BIOPHARMA, INC., Fort Collins, CO (US)

( * ) Notice: Subject to any disclaimer, the term of this patent is extended or adjusted under 35 U.S.C. 154(b) by 139 days.

(21) Appl. No.: 17/226,969

(22) Filed: Apr. 9, 2021

(65) Prior Publication Data

US 2021/0337794 A1    Nov. 4, 2021

Related U.S. Application Data

(63) Continuation of application No. 15/644,646, filed on Jul. 7, 2017, now Pat. No. 11,006,629, which is a continuation-in-part of application No. 15/223,748, filed on Jul. 29, 2016, now Pat. No. 9,844,219, which is a continuation of application No. 14/671,223, filed on Mar. 27, 2015, now Pat. No. 9,468,622, and a continuation of application No. 13/898,126, filed on May 20, 2013, now Pat. No. 9,018,412, which is a continuation of application No. 13/860,680, filed on Apr. 11, 2013, now Pat. No. 9,012,681, which is a continuation of application No. 12/760,940, filed on Apr. 15, 2010, now Pat. No. 8,445,717, which is a continuation-in-part of application No. 12/618,605, filed on Nov. 13, 2009, now Pat. No. 8,426,634.

(60) Provisional application No. 61/199,944, filed on Nov. 20, 2008.

(51) Int. Cl.
| | |
|---|---|
| C07C 407/00 | (2006.01) |
| A01N 37/42 | (2006.01) |
| A61K 45/06 | (2006.01) |
| A61K 33/40 | (2006.01) |
| A61K 31/327 | (2006.01) |
| A61K 31/13 | (2006.01) |
| C07C 409/24 | (2006.01) |
| A01N 59/00 | (2006.01) |
| A61K 31/365 | (2006.01) |
| A61K 31/191 | (2006.01) |

(52) U.S. Cl.
CPC ............ *A01N 37/42* (2013.01); *A01N 59/00* (2013.01); *A61K 31/13* (2013.01); *A61K 31/191* (2013.01); *A61K 31/327* (2013.01); *A61K 31/365* (2013.01); *A61K 33/40* (2013.01); *A61K 45/06* (2013.01); *C07C 407/00* (2013.01); *C07C 409/24* (2013.01); *A01N 2300/00* (2013.01); *C07C 2601/08* (2017.05)

(58) Field of Classification Search
None
See application file for complete search history.

(56) References Cited

U.S. PATENT DOCUMENTS

| | | |
|---|---|---|
| 2,609,391 A | 9/1952 | Greenspan et al. |
| 3,009,468 A | 11/1961 | Eberle |
| 3,365,487 A | 1/1968 | Gonse |
| 4,385,008 A | 5/1983 | Hignett |
| 4,403,994 A | 9/1983 | Hignett |
| 4,483,781 A | 11/1984 | Hartman |
| 5,055,287 A | 10/1991 | Kessler |
| 5,508,046 A | 4/1996 | Cosentino et al. |
| 6,369,288 B1 | 4/2002 | Brown |
| 6,482,786 B1 | 11/2002 | Del Duca et al. |
| 6,491,896 B1 | 12/2002 | Rajaiah et al. |
| 6,492,443 B1 | 12/2002 | Kodemura et al. |
| 7,494,950 B2 | 2/2009 | Armitage et al. |
| 7,628,851 B2 | 12/2009 | Armitage et al. |
| 8,057,595 B2 | 11/2011 | Armitage et al. |
| 9,044,527 B2 | 6/2015 | Neas et al. |
| 9,283,202 B2 | 3/2016 | Neas et al. |
| 9,427,417 B2 | 8/2016 | Myntti |
| 9,844,219 B2 | 12/2017 | Neas et al. |
| 11,006,629 B2 | 5/2021 | Neas et al. |
| 2003/0235623 A1 | 12/2003 | Van Oosterom |
| 2004/0057868 A1 | 3/2004 | McVey et al. |
| 2005/0153857 A1 | 7/2005 | Sherry et al. |
| 2005/0197397 A1 | 9/2005 | Martin |
| 2005/0208094 A1 | 9/2005 | Armitage et al. |
| 2005/0229344 A1 | 10/2005 | Mittelstaedt et al. |

(Continued)

FOREIGN PATENT DOCUMENTS

| | | |
|---|---|---|
| CN | 103843817 A | 6/2014 |
| DE | 202015001904 U1 | 5/2015 |

(Continued)

OTHER PUBLICATIONS

Madronich, S., "Chemical Evolution of Gaseous Air Pollutants Down-Wind of Tropical Megacities: Mexico City Case Study" Atmospheric Environment, 2006, vol. 40, pp. 6012-6018.

(Continued)

*Primary Examiner* — Sudhakar Katakam
*Assistant Examiner* — Jennifer C Sawyer
(74) *Attorney, Agent, or Firm* — Fox Rothschild LLP

(57) ABSTRACT

The present invention relates to antimicrobial, disinfecting, and wound healing compositions and methods for producing and using the same. The compositions may comprise one or more of a peracid, a hydroperoxide, a bis(hydroperoxide), or an epoxide.

6 Claims, 8 Drawing Sheets

(56) References Cited

U.S. PATENT DOCUMENTS

| | | |
|---|---|---|
| 2007/0048175 A1 | 3/2007 | Tichy et al. |
| 2008/0226691 A1 | 9/2008 | Armitage et al. |
| 2009/0144925 A1 | 6/2009 | Orffeo |
| 2010/0016322 A1 | 1/2010 | Nagaraju et al. |
| 2010/0021558 A1 | 1/2010 | Dada et al. |
| 2010/0048763 A1 | 2/2010 | Armitage et al. |
| 2010/0108942 A1 | 5/2010 | Man et al. |
| 2012/0207806 A1 | 8/2012 | LoPesio |
| 2012/0213835 A1 | 8/2012 | Neas et al. |
| 2013/0018097 A1 | 1/2013 | Bolduc et al. |
| 2013/0251590 A1 | 9/2013 | Golden et al. |
| 2013/0330397 A1 | 12/2013 | Neas et al. |
| 2014/0113000 A1 | 4/2014 | Neas et al. |
| 2014/0120179 A1 | 5/2014 | Smith et al. |
| 2014/0249140 A1 | 9/2014 | Niquet et al. |
| 2014/0287154 A1 | 9/2014 | Kaiser et al. |
| 2015/0093425 A1 | 4/2015 | Moore |
| 2015/0133359 A1 | 5/2015 | Molnar et al. |
| 2015/0196526 A1 | 7/2015 | Neas et al. |
| 2016/0174553 A1 | 6/2016 | Matta et al. |
| 2017/0100335 A1 | 4/2017 | Hemmila et al. |
| 2017/0118991 A1 | 5/2017 | Neas et al. |
| 2017/0303538 A1 | 10/2017 | Neas et al. |
| 2020/0129383 A1 | 4/2020 | Neas et al. |
| 2020/0246511 A1 | 8/2020 | Noblitt |
| 2020/0276149 A1 | 9/2020 | Neas et al. |
| 2021/0077438 A1 | 3/2021 | Noblitt et al. |
| 2021/0093602 A1* | 4/2021 | D'Agostino ......... A61K 36/889 |
| 2022/0023174 A1 | 1/2022 | Noblitt et al. |
| 2022/0030871 A1 | 2/2022 | Bui et al. |

FOREIGN PATENT DOCUMENTS

| | | |
|---|---|---|
| EP | 0105689 A2 | 4/1984 |
| EP | 1070505 A1 | 1/2001 |
| EP | 0873687 B1 | 6/2002 |
| EP | 2662330 A1 | 11/2013 |
| EP | 2965624 A1 | 1/2016 |
| EP | 1663333 B1 | 11/2018 |
| FR | 2796286 B1 | 6/2002 |
| GB | 1041983 A | 9/1966 |
| GB | 2278057 A | 11/1994 |
| JP | 60163902 A | 8/1985 |
| JP | 5332679 B2 | 11/2013 |
| WO | 1993001822 A1 | 2/1993 |
| WO | 200233038 A2 | 4/2002 |
| WO | 2004020562 A1 | 3/2004 |
| WO | 2010049892 A2 | 5/2010 |
| WO | 2012128629 A1 | 9/2012 |
| WO | 2014028633 A1 | 2/2014 |
| WO | 2016100818 A1 | 6/2016 |
| WO | 2019010465 A1 | 1/2019 |
| WO | 2019010467 A2 | 1/2019 |
| WO | 2020069079 A1 | 4/2020 |
| WO | 2020252402 A1 | 12/2020 |
| WO | 2021142148 A1 | 7/2021 |
| WO | 2021142152 A1 | 7/2021 |

OTHER PUBLICATIONS

Jacks et al., "Evaluation of Peracid Formation as the Basis for Resistance to Infection in Plants Transformed with Haloperoxidase", Journal of Agricultural and Food Chemistry, 2002, 50: 706-709 (see abstract).

Davies et al., "A convenient preparation of aqueous methyl hydroperoxide and a comparison of its reactivity towards triacetylethylenediamine with that of other nucleophiles: the mechanism of peroxide bleach activation", Journal of Chemical Society, Perkin Transactions 2, 1992, pp. 559-562.

International Search Report and Written Opinion dated Sep. 24, 2018, in Application No. PCT/US2018/041163 (9 pages).

International Search Report and Written Opinion dated Mar. 26, 2021, in Application No. PCT/US2021/012536 (8 pages).

International Search Report and Written Opinion dated Mar. 26, 2021, in Application No. PCT/US2021/012540 (8 pages).

International Search Report and Written Opinion dated Sep. 9, 2020, in Application No. PCT/US2020/037616 (14 pages).

Extended European Search Report dated Mar. 16, 2021 in European Application No. 18828616.5 (8 pages).

Osovsky et al., "Decontamination of Adsorbed Chemical Warfare Agents on Activated Carbon Using Hydrogen Peroxide Solutions", Environmental Sci and Tech (2014), 48:10912-10918.

Alarcon et al., "Antimocrobial properties of magnesium chloride at low pH in the presence of anionic bases", Magnes Res (2014), 27:57-68 (Abstract only).

* cited by examiner

EFFICACY OF PEROXY ALPHA KETO BUTYRIC ACID

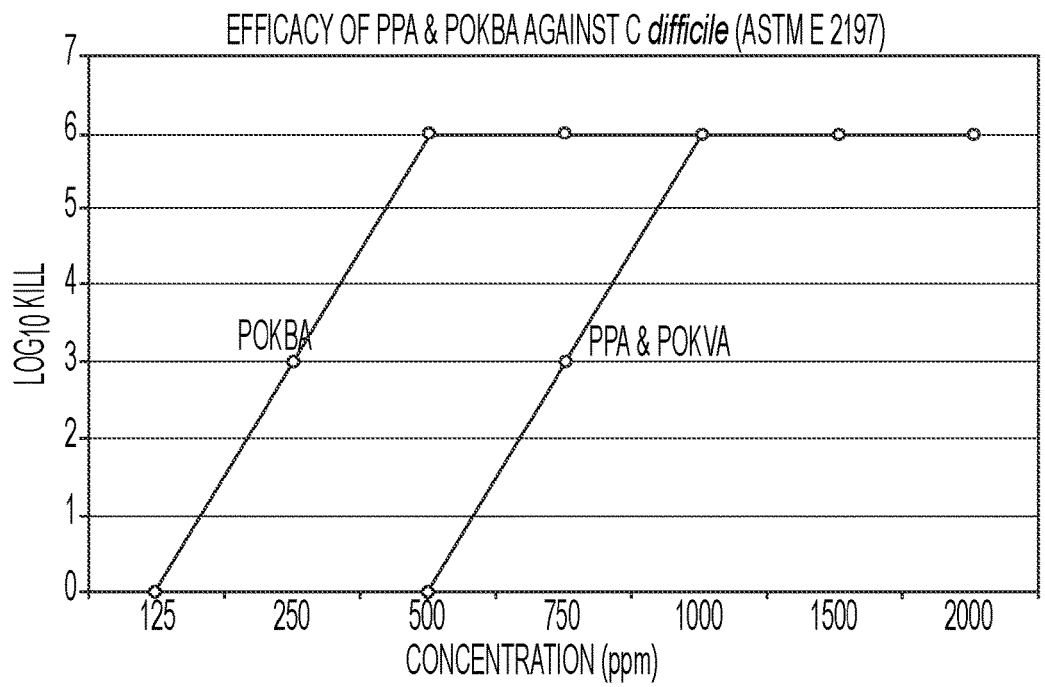

FIG. 3

| | Log Reduction of Bacteria By Disinfectant | | | | | | |
|---|---|---|---|---|---|---|---|
| TEST METHOD | Spray | Spray | Spray | Immersion | Immersion & ASTM-E2107 | Immersion | AOAC 966.04 |
| | Escheria coli | MRSA | Candida albicans | Clostridium sporagenes | Clostridum difficile | Bacillus cereus | Bacillus Subtilis |
| Pyruvic Acid | ≥6.0 | ≥8.0 | ≥6.0 | | | ≥1.5 | |
| Alpha Keto Butyric Acid | ≥6.0 | ≥6.0 | | | | | |
| Alpha Keto Valeric Acid | ≥6.0 | ≥5.7 | | | | | |
| Peroxy Pyruvic Acid | ≥6.0 | ≥6.0 | ≥6.0 | ≥6.0 | ≥6.0 | ≥6.0 | ≥5.0 |
| Peroxy Alpha Keto Butyric Acid | | | | | ≥6.0 | | ≥5.0 |
| Peroxy Alpha Keto Valeric Acid | | | | | ≥6.0 | | |

FIG. 4

ANTIMICROBIAL, DISINFECTING, AND WOUND HEALING COMPOSITIONS AND METHODS FOR PRODUCING AND USING THE SAME

CROSS-REFERENCE TO RELATED APPLICATIONS

This application is a continuation of U.S. patent application Ser. No. 15/644,646, filed Jul. 7, 2017, which was a continuation-in-part of U.S. patent application Ser. No. 15/223,748, filed Jul. 29, 2016, which was a continuation of U.S. patent application Ser. No. 14/671,223, filed Mar. 27, 2015, which was a continuation of U.S. patent application Ser. No. 13/860,680, which was filed Apr. 11, 2013, and a continuation of U.S. patent application Ser. No. 13/898,126, which was filed on May 20, 2013. U.S. patent application Ser. No. 13/860,680 was a continuation of U.S. patent application Ser. No. 12/618,605 (now U.S. Pat. No. 8,426,634), which was filed on Nov. 13, 2009, entitled "α-Keto Peracids and Methods For Producing and Using the Same," and claimed the benefit of U.S. Provisional Patent Application No. 61/199,944, which was filed on Nov. 20, 2008. U.S. patent application Ser. No. 13/898,126, was a continuation of U.S. patent application Ser. No. 12/760,940 (now U.S. Pat. No. 8,445,717), which was filed Apr. 15, 2010, entitled "α-Keto Alkylperacids and Methods for Producing and Using the Same," and was a continuation-in-part of U.S. patent application Ser. No. 12/618,605 (now U.S. Pat. No. 8,426,634), which was filed on Nov. 13, 2009 and claimed the benefit of U.S. Provisional Patent Application No. 61/199,944, which was filed on Nov. 20, 2008. This application claims priority to and the benefit of each of the foregoing applications, all of which are incorporated herein by reference.

FIELD OF THE INVENTION

The present invention relates to antimicrobial, disinfecting, and wound healing compositions and methods for producing and using the same. The compositions may comprise one or more of a peracid, a hydroperoxide, a bis(hydroperoxide), or an epoxide.

BACKGROUND OF THE INVENTION

Human and mammalian health is impacted by the spread of microbial organisms such as viruses, bacteria, and fungi. Microbial organisms continue to cause a variety of sicknesses and ailments. In the wake of widespread microbial organism infections, the public has become even further concerned with sanitization, both of person and property. Consequently, there has been an extensive research on the development of suitable antimicrobial compositions, in particular of antimicrobial compositions that provide immediate and residual kill of microbial organisms.

Currently, there exist several compositions and methods for reducing and/or eliminating microbial organisms from various surfaces. Conventional antimicrobial cleansing products such as hard surface cleaners and surgical disinfectants are typically formulated to provide bacteria removal during washing. Only a few such products have been shown to provide a residual effectiveness against Gram-positive bacteria; however, even such compositions provide only limited residual effectiveness against Gram-negative bacteria. By "residual effectiveness," it is meant that the subject antimicrobial controls microbial growth on a substrate by either preventing growth of microbes or engaging in continuous kill of microbes for some period of time following the washing and/or rinsing process.

Furthermore, many conventional antimicrobial compositions have unpleasant odor or are chemically harsh and can cause irritation. Moreover, most conventional antimicrobial compositions are relatively ineffective against vegetative bacteria that are "dormant." Vegetative bacteria are bacteria or microoganrisms that can grow and reproduce in rich, moist soil where many nutrients are available. The actively growing bacteria in these conditions are referred to as "vegetative cells." Many types of bacteria and fungi can flourish under these conditions. Some examples of bacteria and fungi that can actively reproduce in this kind of soil are *Bacillus, Streptomyces, Pseudomonas, Micrococcus, Mycobacterium*, and *Clostridium. Mycobacterium tuberculosis* can cause the disease tuberculosis, and *Clostridium botulinum* can cause botulism poisoning.

When soil nutrients or moisture are depleted, bacteria from the genus of *Bacillus* and *Clostridium* produce an endospore inside each vegetative cell. Once the vegetative cell (active bacteria) no longer has enough nutrients or moisture to survive, it releases the endospore. The endospore can remain viable for very long periods. When the right conditions return for growth, the endospore creates another vegetative cell, and the bacteria becomes active again. Some fungi produce spores in a similar fashion.

Therefore, there is a need for antimicrobial compositions that are effective against vegetative microbial organisms. There is also a need for antimicrobial compositions that do not have unpleasant odor.

SUMMARY OF THE INVENTION

Some aspects of the invention provide .alpha.-keto alkylperacids and methods for producing and using the same. Such methods typically comprise contacting an .alpha.-keto alkyl-carboxylic acid or a salt thereof with an oxidizing agent without any significant stirring and under conditions sufficient to produce the α-keto alkylperacid. While a variety of oxidizing agents can be used in such methods, typically the oxidizing agent comprises hydrogen peroxide, barium peroxide, sodium carbonate peroxide, calcium peroxide, sodium perborate, lithium peroxide, magnesium peroxide strontium peroxide, zinc peroxide, potassium superoxide, or a mixture thereof. In some embodiments, the reaction temperature is about 10° C. or less. In other embodiments, the reaction temperature ranges from about −30° C. to about 10° C.

Methods of the invention can be used to produce a wide variety of α-keto alkylperacids. In some aspects of the invention, the α-keto alkylperacid is of the formula:

$$\text{HOO—C(=O)—C(=O)—R} \tag{1}$$

or a salt thereof, where R is alkyl of at least two carbon atoms.

In some embodiments, R is $C_2$-$C_{20}$ alkyl. Within these embodiments, in some instances, R is $C_2$-$C_{10}$ alkyl. In some cases, R is selected from the group consisting of ethyl, isopropyl, propyl, butyl, isobutyl, sec-butyl, pentyl, isopentyl, neopentyl, and n-hexyl.

Other aspects of the invention provide methods for reducing the amount of microbe on a surface. Such methods typically include contacting the surface with an antimicrobial solution comprising an effective amount of a compound of Formula I.

In some embodiments, the microbe comprises vegetative bacteria. Within these embodiments, in some instances the microbe comprises bacterial spores, mycobacteria, gram-negative bacteria, vegetative gram-positive bacteria, or a combination thereof.

Still in other embodiments, the antimicrobial solution further comprises hydrogen peroxide.

Yet in other embodiments, the antimicrobial solution comprises at least 40 ppm of the compound of Formula I.

Still other aspects of the invention provide methods for reducing the number of infectious vegetative bacteria on a substrate. Such methods include contacting the substrate with an antimicrobial solution comprising an effective amount of a compound of Formula I.

Yet other aspects of the invention provide methods for preventing and/or reducing bacteria-related diseases in a mammal that result from the mammal's contact with a bacteria-infected substrate. Such methods can include contacting the substrate with a composition comprising of a compound of Formula I.

Other aspects of the invention provide antimicrobial products comprising a compound of Formula I.

In some embodiments, the antimicrobial product is a household care product. Exemplary house hold care products include, but are not limited to, hard surface cleaners, deodorizers, fabric care compositions, fabric cleaning compositions, manual dish detergents, automatic dish detergents, floor waxes, kitchen cleaners, and bathroom cleaners. In some instances, the antimicrobial product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof.

Yet in other embodiments, the antimicrobial product is a medical device disinfectant.

Still in other embodiments, the amount of compound of Formula I that is present in the antimicrobial product is about 100 ppm or less.

Other aspects of the invention provide a method for reducing the amount of microbe on a surface, said method comprising contacting the surface with an antimicrobial solution comprising an effective amount of a compound of Formula I.

In some embodiments, the microbe comprises vegetative bacteria. In other embodiments, the microbe comprises bacterial spores, mycobacteria, gram-negative bacteria, vegetative gram-positive bacteria, or a combination thereof. In one particular embodiment, the microbe comprises bacterial spores.

Still in other embodiments, the antimicrobial solution further comprises hydrogen peroxide. Typically, the antimicrobial solution comprises at least 40 ppm of α-keto alkylperacid. Alternatively, the antimicrobial solution comprises about 4,000 ppm or less, typically 1,000 ppm or less, often 500 ppm or less, more often 100 ppm or less, and still more often 50 ppm or less amount of the compound of Formula I.

The half-life of compound of Formula I in the antimicrobial solution typically is about 120 days or more, often about 180 days or more, and more often about 360 days or more.

Yet other aspects of the invention provide a method for reducing the number of infectious vegetative bacteria on a substrate comprising contacting the substrate with an antimicrobial solution comprising an effective amount of a compound of Formula I. Other aspects of the invention provide a method for reducing the number of bacterial spores on a substrate comprising contacting the substrate with an antimicrobial solution comprising an effective amount of a compound of Formula I.

Further aspects of the invention provide methods for preventing and/or reducing bacteria-related diseases in a mammal that result from the mammal's contact with a bacteria-infected substrate. Such methods comprise contacting the substrate with a composition comprising a compound of Formula I prior to allowing the mammal to come in contact with the substrate.

Still other aspects of the invention provide an antimicrobial product comprising a compound of Formula I. In some embodiments, the product is a household care product. Within such embodiments, in some cases the house hold care product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. In other embodiments, the antimicrobial product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. Antimicrobial products of the invention can be used in a wide variety of settings including, but not limited to, in health care facilities such as hospitals, rehabilitation, assisted living facilities, etc.

In other embodiments, the antimicrobial product is a medical device disinfectant. Still in other embodiments, the antimicrobial product is used as a disinfectant for aseptic filling equipment. Yet in other embodiments, the antimicrobial product is used in an aseptic food processing system. In other embodiments, the antimicrobial product is used as a disinfectant for biofilms in water systems. Still in other embodiments, the antimicrobial product is used as a disinfectant for waste water treatment.

In some embodiments, the amount of compound of Formula I present in the antimicrobial product is about 100 ppm or less. Still in other embodiments, the half-life of a compound of Formula I is at least 20 days.

In another aspect, the present invention relates to novel antimicrobial, disinfecting, and/or wound healing compositions and methods for producing and using the same. The compositions may comprise one or more of a keto acid, a peroxyacid, a hydroperoxide, a bis(hydroperoxide), or an epoxide.

In another aspect, the present invention provides a wound healing composition comprising 3,3-bis(hydroperoxy)butanoic acid, 3,3-bis(hydroperoxy)butaneperoxoic acid, or 3-oxobutaneperoxoic acid, or a mixture thereof. In other embodiments, the compositions further comprise 5-hydroperoxy-5-methyl-1,2-dioxolan-3-one. In some embodiments, the composition further comprises one or more of hydrogen peroxide, an organic hydroperoxide, an organic peroxide, an organic peracid, an inorganic peracid, an organic acid, or an inorganic acid. In some embodiments, the composition further comprises hydrogen peroxide.

In some embodiments, the present invention provides a wound healing composition comprising acetoacetic acid, or a salt of acetoacetic acid. The salt of acetoacetic acid may be a lithium, sodium, potassium, rubidium, cesium, magnesium, or calcium salt. The composition may further comprise a hydroperoxide, including hydrogen peroxide and/or an organic hydroperoxide. In other embodiments, the composition may further comprise a keto acid. The keto acid may be an alpha-, beta-, or gamma-keto acid. In some embodiments, the composition may further comprise pyruvic acid, parapyruvic acid, or citramalic acid, any of their salts, or mixtures thereof. In other embodiments, the composition may further comprise an acetoacetate ester such as methyl acetoacetate, ethyl acetoacetate, or acetoacetic anhydride. In some embodiments, the composition further comprises hydrogen peroxide.

In some embodiments, the present invention provides a wound healing composition comprising hydroperoxyacetic acid. In other embodiments, the composition further comprises hydrogen peroxide.

In one aspect, the present invention provides a wound healing composition made by a method comprising contacting a keto acid or a salt or anhydride thereof with an oxidizing agent while stirring and under conditions sufficient to produce one or more of a peroxyacid, a hydroperoxide, a bis(hydroperoxide), or an epoxide. In some embodiments, the conditions are sufficient to produce a peroxyacid and a bis(hydroperoxide). In some embodiments, the conditions are sufficient to produce a peroxyacid, a hydroperoxide, a bis(hydroperoxide), and an epoxide.

In some embodiments, the keto acid may be an alpha-, beta-, or gamma-keto acid. In other embodiments, the keto acid is an alpha-keto acid. In some embodiments, the keto acid is pyruvic acid or a salt or anhydride thereof. In other embodiments, the keto acid is parapyruvuc acid or a salt or anhydride thereof. In other embodiments, the keto acid is acetoacetic acid or a salt or anhydride thereof. In some embodiments, the keto acid salt may be a lithium, sodium, potassium, rubidium, cesium, magnesium, or calcium salt, or a mixture thereof. In other embodiments, the process further comprises contacting the keto acid or salt thereof and the oxidizing agent with maleic acid or anhydride, citraconic acid or anhydride, or a mixture thereof.

In some embodiments, the reaction temperature is about 10° C. or less. In other embodiments, the reaction temperature ranges from about –30° C. to 10° C. In some embodiments, the molar ratio of oxidizing agent to keto acid typically ranges from 1:1 to about 4:1.

In one embodiment, the method comprises stirring the oxidizing agent at a shear rate between 150 s$^{-1}$ and 850 s$^{-1}$, cooling the oxidizing agent to between –10° C. to 0° C., and adding the keto acid at a rate sufficient to maintain the temperature between –10° C. to 0° C. during addition of the keto acid to form a reaction solution. A shear rate between about 150 and about 850 sec$^{-1}$ equates to stirring at a rate between about 90 and about 500 RPM. In some embodiments, the method further comprises continually stirring the reaction solution for 10 to 12 hours at a temperature of –10° C. to 0° C. In other embodiments, the method further comprises warming the reaction solution to between 14° C. and 27° C. In some embodiments, the method further comprises cooling the reaction solution to maintain this temperature for 30 days. In some embodiments, the oxidizing agent is hydrogen peroxide and the keto acid is pyruvic acid.

In another aspect, the present invention provides a wound healing composition made by a method comprising contacting citramalic acid or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the citramlic acid salt may be a lithium, sodium, potassium, rubidium, cesium, magnesium, or calcium salt, or a mixture thereof. In other embodiments, the process further comprises contacting citramalic acid or salt thereof and the oxidizing agent with acetic acid or anhydride thereof, maleic acid or anhydride thereof, citraconic acid or anhydride thereof, or a mixture thereof.

In another aspect, the present invention provides a wound healing composition made by a method comprising contacting an acetoacetate ester or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the acetoacetate ester may be methyl acetoacetate or ethyacetoacetate, or a mixture thereof. In other embodiments, the acetoacetate ester salt may be a lithium, sodium, potassium, rubidium, cesium, magnesium, or calcium salt, or a mixture thereof. In some embodiments, the process further comprises adding citramalic acid.

While a variety of oxidizing agents may be used in such methods, typical oxidizing agents may comprise hydrogen peroxide, barium peroxide, sodium carbonate peroxide, potassium superoxide, or a mixture thereof. In some embodiments, the oxidizing agent is hydrogen peroxide.

In another aspect, the present invention provides an wound healing composition comprising a peroxyacid and a bis(hydroperoxide). In some embodiments, the composition further comprises a hydroperoxide. In other embodiments, the composition further comprises an epoxide. In some embodiments, the composition comprises peracetic acid and 3,3-bis(hydroperoxy)butanoic acid. In other embodiments, the composition comprises peracetic acid and 3,3-bis(hydroperoxy)butaneperoxoic acid. In other embodiments, the composition further comprises at least one of methylhydroperoxide and hydroxymethyl hydroperoxide. In some embodiments, the composition further comprises 5-hydroperoxy-5-methyl-1,2-dioxolan-3-one. In some embodiments, the composition further comprises hydrogen peroxide.

In some embodiments, the wound healing composition further comprises peroxycitraconic acid. The peroxycitraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the compositions may comprise diperoxycitraconic acid, i.e., (2Z)-2-methylbut-2-enediperoxoic acid. In other embodiments, the antimicrobial composition further comprises peroxycitramalic acid. The peroxycitramalic acid may be either 4-hydroperoxy-2-hydroxy-2-methyl-4-oxobutanoic acid, 4-hydroperoxy-3-hydroxy-3-methyl-4-oxobutanoic acid, or a mixture thereof.

In another aspect, the present invention provides an antimicrobial, chemical oxidizer, or disinfecting products comprising one or more of the above-described compositions. In some embodiments, the antimicrobial product is a household care product. Within such embodiments, in some cases the house hold care product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. In other embodiments, the antimicrobial product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. Antimicrobial products of the invention can be used in a wide variety of settings including, but not limited to, in health care facilities such as hospitals, rehabilitation, assisted living facilities, etc.

In other embodiments, the antimicrobial product is a medical device disinfectant. Still in other embodiments, the antimicrobial product is used as a disinfectant for aseptic filling equipment. Yet in other embodiments, the antimicrobial product is used in an aseptic food processing system. In other embodiments, the antimicrobial product is used as a disinfectant for biofilms in water systems. Still in other embodiments, the antimicrobial product is used as a disinfectant for waste water treatment.

In yet another aspect the present invention provides a method of making a wound healing composition comprising contacting a keto acid or a salt or anhydride thereof with an oxidizing agent while stirring and under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide.

In some embodiments, the keto acid may be an alpha-, beta-, or gamma-keto acid. In some embodiments, the keto acid is pyruvic acid or a salt or anhydride thereof. In other embodiments, the keto acid is parapyruvuc acid or a salt or anhydride thereof. In other embodiments, the keto acid is acetoacetic acid or a salt or anhydride thereof. In some embodiments, the keto acid salt may be a lithium, sodium, potassium, rubidium, cesium, magnesium, or calcium salt, or a mixture thereof. In other embodiments, the process further comprises contacting the keto acid or salt thereof and the oxidizing agent with maleic acid or anhydride, citraconic acid or anhydride, or a mixture thereof.

In some embodiments, the reaction temperature is about 10° C. or less. In other embodiments, the reaction temperature ranges from about −10° C. to 10° C. In some embodiments, the ratio of oxidizing agent to keto acid typically ranges from 1:1 to about 4:1. In some embodiments, the stirring is at a shear rate between 150 s$^{-1}$ and 850 s$^{-1}$. A shear rate between about 150 and about 850 sec$^{-1}$ equates to stirring at a rate between about 90 and about 500 RPM.

In one embodiment, the method comprises stirring the oxidizing agent at a shear rate between 150 s$^{-1}$ and 850 s$^{-1}$, cooling the oxidizing agent to between −10° C. to 0° C., and adding the keto acid at a rate sufficient to maintain the temperature between −10° C. to 0° C. during addition of the keto acid to form a reaction solution. A shear rate between about 150 and about 850 sec$^{-1}$ equates to stirring at a rate between about 90 and about 500 RPM. In some embodiments, the method further comprises continually stirring the reaction solution for 10 to 12 hours. In other embodiments, the method further comprises warming the reaction solution to between 14° C. and 27° C. In some embodiments, the method further comprises cooling the reaction solution to maintain this temperature for 30 days. In some embodiments, the oxidizing agent is hydrogen peroxide and the keto acid is pyruvic acid.

In another aspect, the present invention provides a method of making a wound healing composition comprising contacting citramalic acid or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the citramlic acid salt may be a lithium, sodium, potassium, rubidium, cesium, magnesium, or calcium salt, or a mixture thereof. In other embodiments, the process further comprises contacting citramalic acid or salt thereof and the oxidizing agent with acetic acid, maleic acid or anhydride, citraconic acid or anhydride, or a mixture thereof.

In another aspect, the present invention provides a method of making a wound healing composition comprising contacting an acetoacetate ester or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the acetoacetate ester may be methyl acetoacetate or ethyacetoacetate, or a mixture thereof. In other embodiments, the acetoacetate ester salt may be a lithium, sodium, potassium, rubidium, cesium, magnesium, or calcium salt, or a mixture thereof. In some embodiments, the process further comprises adding citramalic acid.

While a variety of oxidizing agents may be used in such methods, typical oxidizing agents may comprise hydrogen peroxide, barium peroxide, sodium carbonate peroxide, potassium superoxide, or a mixture thereof. In some embodiments, the oxidizing agent is hydrogen peroxide.

In another aspect, the present invention provides a method of making a wound healing composition comprising combining one or more of a peroxyacid, a hydroperoxide, a bis(hydroperoxide), or an epoxide in an aqueous solution. In some embodiments the method comprises combining a peroxyacid and bis(hydroperoxide) in an aqueous solution. In some embodiments, the peroxyacid is peracetic acid. In other embodiments, the bis(hydroperoxide) is 3,3-bis(hydroperoxy)butanoic acid or 3-bis(hydroperoxy)butaneperoxoic acid.

In some embodiments, the method further comprises adding a hydroperoxide to the aqueous solution. In some embodiments, the hydroperoxide is one of methylhydroperoxide and hydroxymethyl hydroperoxide. In other embodiments, the method further comprises adding an epoxide to the aqueous solution. In some embodiments, the epoxide is 5-hydroperoxy-5-methyl-1,2-dioxolan-3-one. In some embodiments, the method further comprises adding hydrogen peroxide to the aqueous solution.

In other embodiments, the peroxyacid is peroxycitraconic acid. The peroxycitraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the peroxyacid is diperoxycitraconic acid, i.e., (2Z)-2-methylbut-2-enediperoxoic acid. In other embodiments, the peroxyacid is peroxycitramalic acid. The peroxycitramalic acid may be either 4-hydroperoxy-2-hydroxy-2-methyl-4-oxobutanoic acid, 4-hydroperoxy-3-hydroxy-3-methyl-4-oxobutanoic acid, or a mixture thereof.

In another aspect, the present invention provides methods of making antimicrobial, chemical oxidizer, and disinfecting solutions comprising any of the above-described methods.

In another aspect, present invention provides methods for treating a wound infection in a subject comprising contacting the infected wound in the subject with a therapeutically effective amount of an above-described composition. Methods of the invention can be used to treat surgical wound, battle wound, accidental wound, thermal burn wound, chemical burn wound, chronic wound, decubitus ulcer, foot ulcer, venous ulcer, laser treatment wound, sunburn, and/or an abrasion.

Generally, the composition is applied to the infected wound at least once, often at least twice a day initially.

In other embodiments, the composition is formulated as a gel, a liquid, lotion, skin patch, irrigation gel, a liquid, lotion, skin patch, a spray, application granules, or a combination thereof.

In yet another aspect, the present invention provides methods for reducing the amount of microbes on a surface. Such methods typically include contacting the surface with an antimicrobial product comprising an above-described composition. Yet other aspects of the invention provide a method for reducing the number of infectious vegetative bacteria on a substrate comprising contacting the substrate with an antimicrobial solution comprising an effective amount of an above-described composition. Other aspects of the invention provide a method for reducing the number of bacterial spores on a substrate comprising contacting the substrate with an antimicrobial solution comprising an effective amount of an above-described composition.

In some embodiments, the microbe comprises vegetative bacteria. Within these embodiments, in some instances the microbe comprises bacterial spores, mycobacteria, gram-negative bacteria, vegetative gram-positive bacteria, or a combination thereof.

Yet other aspects of the invention provide methods for preventing and/or reducing bacteria-related diseases in a mammal that result from the mammal's contact with a bacteria-infected substrate. Such methods can include contacting the substrate with an above-described composition.

The details of one or more embodiments of the invention are set forth in the description below. Other features, objectives, and advantages of the invention will be apparent from the description and from the claims.

BRIEF DESCRIPTION OF THE FIGURES

The accompanying drawings, which are incorporated herein and constitute part of this specification, illustrate the presently preferred embodiments of the invention, and, together with the general description above and the detailed description given below, serve to explain the features of the invention. In the drawings:

FIG. 3 is a graph showing comparison of effectiveness against *C. difficile* between peroxy pyruvic acid and peroxy α-ketobutyric acid.

FIG. 4 is a table showing effectiveness of antimicrobial activities of various carboxylic acids and peroxy α-keto carboxylic acids against various microorganisms.

DETAILED DESCRIPTION OF THE INVENTION

Figure 1:
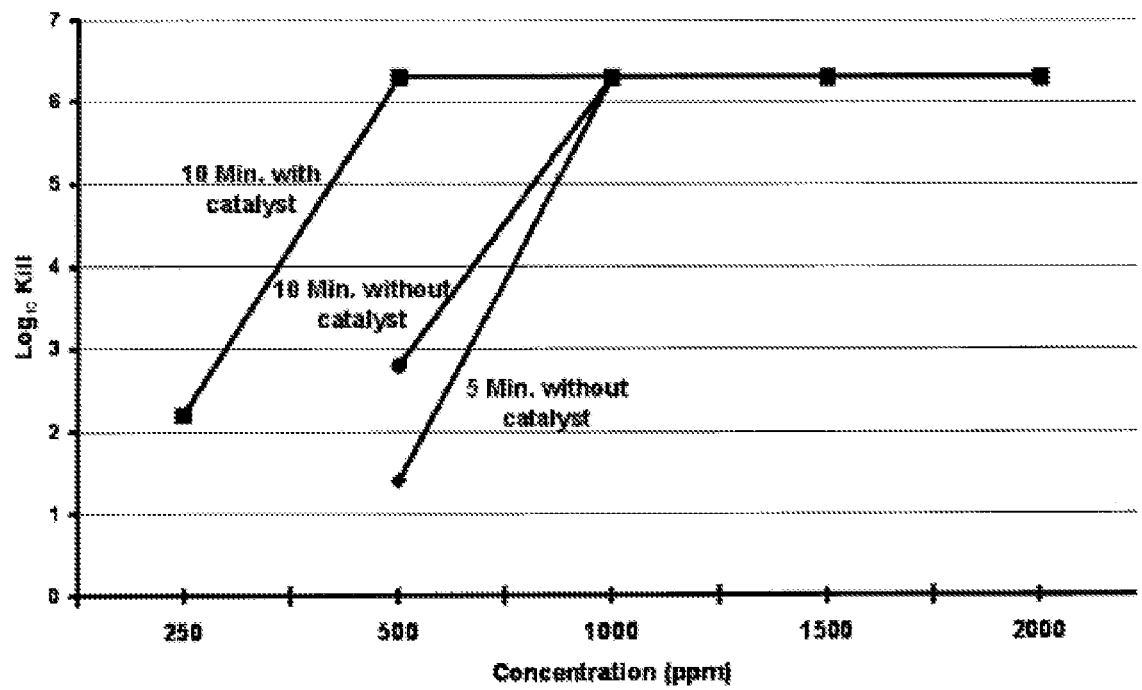
FIG. 1 shows graph of efficacy of peroxy α-keto pyruvic acid against *C. difficile* with or without a catalyst.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers expressing quantities of ingredients, dimensions, reaction conditions, and so forth, used in the specification and claims, are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Some aspects of the invention provide α-keto alkylperacids and methods for producing and using the same. As used herein, the terms "α-keto alkylperacid" and "α-keto alkylperoxyacid" are used interchangeably herein and refer to a compound of the formula: HOO—C(=O)—C(=O)—R, or a salt thereof, where R is alkyl of at least two carbon atoms. The term alkyl refers to a saturated linear monovalent hydrocarbon moiety of two to twenty, typically two to ten, and often two to eight carbon atoms or a saturated branched monovalent hydrocarbon moiety of three to twenty, typically three to ten, and often three to eight carbon atoms. Exemplary alkyl group include, but are not limited to, ethyl, n-propyl, 2-propyl, tert-butyl, pentyl, and the like.

Peracids or peroxyacids refer to carboxylic acids in which the acidic —OH group has been replaced by an —OOH group. They are strong oxidizing agents and are generally unstable. They are most often used as oxidizing agents in various chemical reactions. Peroxy acids are generally not very stable even in solution and decompose to their corresponding carboxylic acid and oxygen. Because most peracids decompose relatively quickly under ambient conditions, they are typically not used for any other purposes except in chemical reactions. Even then, many peroxyacids are synthesized just prior to their use. Some peroxyacids, for example, meta-chloroperoxybenzoic acid (MCPBA), are somewhat stable at a lower temperature as long as they are not in a pure form. Pure MCPBA can be detonated by shock or by sparks. It is, therefore, commercially sold as a much more stable mixture that is less than 72% pure.

Typically, peroxyacids are prepared by electrolytic oxidation of ordinary carboxylic acids or by using a transition metal catalyst and an oxidizing agent or by using a very strong oxidizing agent. In electrolytic oxidation, typically a high current density must be used to form the peroxyacid in good yield. Such use of a high current density typically increases the cost of producing peroxyacids.

As used herein, "peracid," "peroxyacid," "percarboxilic," and "peroxycarboxilic acid," and are used interchangeably herein and refer to a compounds generally have the formula $R(CO_3H)_n$, where, for example, R is an alkyl, arylalkyl, cycloalkyl, aromatic, or heterocyclic group, and n is one, two, or three, and named by prefixing the parent acid with "peroxy-." The R group can be saturated or unsaturated as well as substituted or unsubstituted. Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof. In some embodiments, the compositions of the invention utilize a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the peroxycarboxylic acid is peracetic acid (C2), peroxy propionic acid (C3), peroxybutanoic acid (C4), peroxisuccinic and peroxymalonic acid. It should be noted that both the peroxysuccinic and peroxymalonic acid may come from the alpha-keto dicarboxylic acids. Furthermore, because these acids exist in the Krebs cycle they are metabolically active.

In some embodiments, the compositions and methods of the present invention include peroxyacetic acid. Peroxyacetic (or peracetic) acid is a peroxycarboxylic acid having the formula: $CH_3COOH$. Generally, peroxyacetic acid is a liquid having an acrid odor at higher concentrations and is freely soluble in water, alcohol, ether, and sulfuric acid.

Peroxyacids can also be produced using a transition metal catalyst and an oxidizing agent or simply by using a strong oxidizing agent. Unfortunately, use of a strong oxidizing agent in and of itself creates potentially dangerous conditions and increases the high cost of peroxyacid production. And use of a transition metal catalyst render the resulting peroxyacid often contaminated with the transition metal.

Some methods of the invention for producing α-keto alkylperacids include contacting an α-keto alkylcarboxylic acid or a salt thereof with an oxidizing agent without any significant stirring and under conditions sufficient to produce the α-keto alkylperacid. Typically, the reaction condition comprises non-stirring conditions where a mixture of the α-keto alkylcarboxylic acid and the oxidizing agent is simply allow to stand without any stirring. As used herein, unless the context requires otherwise, the term "stir" or "stirring" refers to agitating or act of causing a mixing of the reagents by using an external force such as by using a mechanical stirrer, a magnetic stirrer, a shaker, or any other mechanical, electrical, magnetic, or manual force including simply mixing the reagents manually (e.g., by stirring or shaking).

Surprisingly and unexpectedly, the present inventors have found that by contacting an α-keto alkylcarboxylic acid and an oxidizing agent and letting the mixture stand without any significant mixing, a good yield of the corresponding α-keto alkylperoxyacid can be produced. Generally, the yield of the reaction is at least 5%, typically at least 8%, and often at least 12%.

It should be noted that the yield of the α-keto alkylperoxyacid is affected by a variety of reaction conditions and reagents used. One of the factors influencing the yield of α-keto alkylperoxyacid is the reaction temperature. Generally, the rate of reaction increases as the temperature increases. However, a higher reaction temperature can also increase the yield of side-product(s) and/or decomposition of the α-keto alkylperoxyacid that is formed. Therefore, the reaction temperature is typically kept at about 10° C. or below, often at about 4° C. or below, and more often at about ~10° C. or below.

The concentration of the reagents can also affect the rate and the yield of α-keto alkylperoxyacid. The initial concentration of the oxidizing agent is generally about 18 M or less, typically about 7 M or less, and often about 1 M or less.

The reaction time can also affect the yield of α-keto alkylperoxyacid. Typically the reaction time ranges from about 4 hours to about 12 hours, often from about 6 hours to about 8 hours, and more often from about 10 hours to about 12 hours.

Methods of the invention are applicable to a wide variety of α-keto alkylcarboxylic acids. Generally any α-keto alkylcarboxylic acid can be used to produce the corresponding α-keto alkylperoxyacid. Exemplary α-keto carboxylic acids include, but are not limited to, α-keto butyric acid, α-keto valeric acid, α-keto hexanoic acid, etc.

Exemplary oxidizing agents that are useful in methods of the invention include, but are not limited to, hydrogen peroxide, barium peroxide, sodium carbonate peroxide, calcium peroxide, sodium perborate, lithium peroxide, magnesium peroxide strontium peroxide, zinc peroxide, potassium superoxide, and the like.

When describing a chemical reaction, the terms "treating," "contacting," and "reacting" are used interchangeably herein, and refer to adding two or more reagents under appropriate conditions to produce the indicated and/or the desired product. It should be appreciated that the reaction which produces the indicated and/or the desired product may not necessarily result directly from the combination of reagents which were initially added, i.e., there may be one or more intermediates which are produced in the mixture which ultimately leads to the formation of the indicated and/or the desired product.

The reaction is generally conducted in an aqueous solution. Other solvents, such as an organic solvent can also be used in addition to or in place of the aqueous solution. Because it is inexpensive and commercially available in an aqueous solution, typically hydrogen peroxide is used as an oxidizing agent.

The ratio of oxidizing agent to α-keto alkylcarboxylic acid typically ranges from about 0.5:1 to about 2:1, often about 2:1 to about 6:1.

In another aspects, the present invention relates to antimicrobial, disinfecting, and/or wound healing compositions comprising one or more of a keto acid, a peracid, a hydroperoxide, a bis(hydroperoxide), or an epoxide and methods for producing and using the same.

Some methods of the invention include contacting a keto acid and oxidizing agent while stirring and under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide.

It should be noted that the yield of the reaction is affected by a variety of reaction conditions and reagents used. One of the factors influencing the yield is the reaction temperature. Generally, the rate of reaction increases as the temperature increases, however, a higher reaction temperature can also increase the yield of side-product(s) and/or decomposition to the non a-keto peroxyacid. Therefore, the reaction temperature is typically kept at about 0° C. or below, often at about 10° C. or below, and more often at about −20° C. or below. In some embodiments, the reaction temperature is between −10° C. to 10° C.

The concentration of the reagents can also affect the rate and the yield of the reaction. The initial concentration of the oxidizing agent is generally about 18 M or less, typically about 7 M or less, and often about 1 M or less.

The reaction time can also affect the yield. Typically the reaction time ranges from about 4 hours to about 12 hours, often from about 6 hours to about 8 hours, and more often from about 10 hours to about 12 hours.

Methods of the invention are applicable to a wide variety of keto acids, and in particular alpha-keto carboxylic acids. In fact, generally any alpha-keto carboxylic acid can be used as long as any reactive functional group within the a-keto carboxylic acid is properly protected. Suitable protection groups for various chemical reactions are well known to one skilled in the art. See, for example, Protective Groups in Organic Synthesis, 3rd edition, T. W. Greene and P. G. M. Wuts, John Wiley & Sons, New York, 1999; Smith and March, Advanced Organic Chemistry, 5th ed., John Wiley & Sons, New York, N.Y., 2001; and Harrison and Harrison et al., Compendium of Synthetic Organic Methods, Vols. 1-8 (John Wiley and Sons, 1971-1996), which are incorporated herein by reference in their entirety. Exemplary a-keto carboxylic acids include, but are not limited to, pyruvic acid, a-keto butyric acid, a-keto valeric acid, a-keto glutaric acid, 2-oxo cylopental acetic acid, etc.

In some embodiments, the methods may comprise additional reagents such as acetic acid or anhydride, maleic acid or anhydride, citraconic acid or anhydride, or a mixture thereof.

In an exemplary embodiment, the method comprises contacting a mixture of pyruvic acid, maleic acid, and citraconic acid with hydrogen peroxide while stirring at a reaction conditions sufficient to produce the reaction products shown in the reaction schemes of FIGS. 5-8.

When describing a chemical reaction, the terms "treating," "contacting," and "reacting" are used interchangeably herein, and refer to adding two or more reagents under appropriate conditions to produce the indicated and/or the desired product. It should be appreciated that the reaction which produces the indicated and/or the desired product may not necessarily result directly from the combination of reagents which were initially added, i.e., there may be one or more intermediates which are produced in the mixture which ultimately leads to the formation of the indicated and/or the desired product.

The reaction is generally conducted in an aqueous solution. Other solvents, such as an organic solvent can also be used in addition to or in place of the aqueous solution. Because it is inexpensive and commercially available in an aqueous solution, typically hydrogen peroxide is used as an oxidizing agent.

The ratio of oxidizing agent to keto acid typically ranges from about 0.5:1 to about 2:1, often about 2:1 to about 6:1.

Some aspects of the invention disclose a process for forming a stable aqueous composition containing one or more of a peroxyacid, a hydroperoxide, a bis(hydroperoxide), or an epoxide. In some embodiments, the invention discloses a process for forming a stable aqueous composition comprising a peroxyacid and a bis(hydroperoxide). In some embodiments, the invention discloses a process for forming a stable aqueous composition comprising a peroxyacid, a hydroperoxide, a bis(hydroperoxide), and an epoxide.

In some embodiments, the compositions comprise acetoacetic acid. Acetoacetic acid is one of the ketone bodies (along with 3-hydroxybutyric acid and acetone, although acetone is just a byproduct), which are major energy sources for the body, particularly during starvation. Ketone bodies are involved in pathways related to the Kreb's cycle, lipogenesis, sterol biosynthesis, glucose metabolism, (β-oxidation of fatty acids, mitochondrial electron transport chain, intracellular signal transduction pathways, hormonal signaling, and the microbiome (Cotter, D. G., et al., *Am. J. Physiol, Heart Circ. Physiol.*, 2013, 304, H1060-H1076). It has been tied to skin formation/biosynthesis in rats (Edmond, J., *J. Biol. Chem.*, 1974, 249, 72-80). Additionally, it was just recently found to upregulate osteoblasts and increase bone formation (Saito, A., et al. *Biochem. Biophys. Res. Comm.*, 2016, 473, 537-544).

Because acetoacetic acid can be converted into acetyl-CoA in vivo, its ability to affect biological processes is extremely high. However, its presence in the solution is unexpected because acetoacetic acid is an unstable compound that reacts intramolecularly and irreversibly, producing acetone and carbon dioxide. Thus, it is expected to be unstable in all solvents and even as a solid compound. However, acetoacetic acid represents a rather unique case where a compound is stabilized by the addition of hydrogen peroxide, whereas normally the addition of a peroxide leads to chemical oxidation/degradation. This stabilization is caused by the formation of a range of possible peroxide "adducts" with its ketone functionality and possibly its carboxylic acid. Because both moieties are required for intramolecular "self-destruction", the formation of these other forms slows down the decomposition of the compound. Peroxide adducts may include 3,3-bis(hydroperoxy) butanoic acid, 3,3-bis(hydroperoxy)butaneperoxoic acid, 3-oxobutaneperoxoic acid, and 5-hydroperoxy-5-methyl-1, 2-dioxolan-3-one. This stabilization is shown in the reaction scheme of FIG. 6. These compositions may be further stabilized by citramalic acid or an acetoacetate ester, such as methyl acetoacetate or ethyl acetoacetate.

In some embodiments, the compositions may comprise peroxycitraconic acid. The peroxycitraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the compositions may comprise diperoxycitraconic acid, i.e., (2Z)-2-methyl-but-2-enediperoxoic acid. In other embodiments, the antimicrobial composition further comprises peroxycitramalic acid. The peroxycitramalic acid may be either 4-hydroperoxy-2-hydroxy-2-methyl-4-oxobutanoic acid, 4-hydroperoxy-3-hydroxy-3-methyl-4-oxobutanoic acid, or a mixture thereof.

Additionally, it was particularly unexpected that stable compositions of peracids and bis(hydroperoxides) could be prepared, since peracids are very strong oxidizing agents even at a pH of 2 to 8 because the water soluble peracids are decomposing to form free radicals.

For the purpose of this invention a "stable" composition is one which maintains sufficient physical properties and active oxygen content long enough to be useful, about twelve months. One important factor that is that "stable" does not imply static. That is, compositions of the present invention may be constantly undergoing a series of internal reactions. This is true of all liquid solutions to a degree, particularly for aqueous ones. However, this is especially true for compositions of the present invention, which have a large number of reversible and effectively irreversible reactions occurring at all times.

While various reaction parameters are disclosed herein, it should be appreciated that the scope of the invention is not limited to these particular reaction parameters.

Various embodiments of the disclosure could also include permutations of the various elements recited in the claims as if each dependent claim was a multiple dependent claim incorporating the limitations of each of the preceding dependent claims as well as the independent claims Such permutations are expressly within the scope of this disclosure.

While various reaction parameters are disclosed herein, it should be appreciated that the scope of the invention is not limited to these particular reaction parameters.

Utility

Compounds and compositions or the invention can be used as a disinfectant. As used herein, the term "disinfection" refers to removal, destruction, killing, or reducing of at least a significant portion of a pathogenic microorganism population from a surface of an object. Typically, methods, compounds and compositions of the invention can be used to reduce at least about 90%, often at least about 95%, more often at least about 98%, still more often at least about 99.9% and most often all of the microorganism population from a surface. Moreover, in contrast to most commercial antimicrobial compounds that are used as disinfectants, compounds and compositions of the invention have been found to be also effective against bacterial spores.

Disinfection is often done to protect the integrity of bacteriological test results (for example, test done for health screening of patients) and/or to prevent the occurrence and spread of disease resulting from inability to control the pathogenic microorganism population. As used herein, the term "microorganism" includes bacteria, virus, fungi, algae, prion, and other pathogenic organisms known to one skilled in the art. Typically, the term microorganism refers to bacteria. Physical sterilization—for example, applying steam or other gas via pressurized autoclave—is generally not feasible for disinfection of large spaces and surfaces or sensitive medical equipment. In addition, physical sterilization is inapplicable for protecting the integrity of test results. Moreover, physical sterilization cannot be used on delicate or temperature-sensitive instruments and devices.

Human and mammalian health is impacted by the spread of microbial entities at home, school, work, and in the environment generally. As stated above, conventional methods of disinfection or cleaning and sanitizing various equipment and areas require very high temperatures up to 185° F. or the use of a relatively harsh antimicrobial compound. Unfortunately, the majority of conventional chemical disinfecting agents are useful for reducing only gram-positive bacteria.

Bacteria found on human skin are typically divided into two groups, namely, resident and transient bacteria. Resident bacteria are Gram-positive bacteria that establish as permanent microcolonies on the surface and outermost layers of the skin. Such bacteria play a fundamental role in preventing the colonization of other, more harmful bacteria and fungi. Transient bacteria are bacteria that are not part of the normal resident of the flora of the skin. Rather, transient bacteria are deposited when airborne contaminated material lands on the skin or when contaminated material is brought into physical contact with such bacteria. Transient bacteria are typically divided into two subgroups: Gram-positive and Gram-negative. Gram-positive bacteria include pathogens such as *Staphylococcus aureus, Streptococcus pyogenes* and *Clostridium botulinum*. Gram-negative bacteria include pathogens such as *Salmonella, Escherichia coli, Klebsiella, Haemophilus, Pseudomonas aeuginosa, Proteus* and *Shigella dysenteriae*. Gram-negative bacteria are generally distinguished from Gram-positive bacteria via the existence of an additional protective cell membrane in the former, which often results in Gram-negative bacteria being less susceptible to conventional, topical antibacterial actives.

As stated above, there exist several compositions and methods for reducing and/or eliminating the formation of bacteria and/or viruses. For example, it is well known that the washing of hard surfaces, food (e.g., fruit or vegetables) and skin, especially the hands, with antimicrobial or non-medicated soap, is effective against viruses and bacteria. Often removal of the viruses and bacteria is due to the surfactant activity of the soap and the mechanical action of the wash procedure, rather than the function of an antimicrobial agent. Thus, it is recommended that people wash frequently to reduce the spread of viruses and bacteria. However, many conventional products and methods of sanitization, including washing, fail to address the dilemma of sanitization "on the go," that is to say, when a consumer is removed from the benefit of running water. Those skilled in the art have attempted to resolve this dilemma via the incorporation of antimicrobial agents into disinfecting lotions, cleansing wipes and the like. Such articles reduce the need for water during or following the application of the subject composition.

Other conventional antimicrobial cleansing products include deodorant soaps, hard surface cleaners, and surgical disinfectants. These traditional, rinse-off antimicrobial products have been formulated to provide bacteria removal during washing. A few such products, including antimicrobial soaps, have also been shown to provide a residual effectiveness against Gram-positive bacteria, but provide limited residual effectiveness against Gram-negative bacteria. By "residual effectiveness," it is meant that the antimicrobial agent controls microbial growth on a substrate by either preventing growth of microbes or engaging in continuous kill of microbes for some period of time following the washing and/or rinsing process. To address the dilemma of limited residual efficacy against Gram-negative bacteria, some have sought to incorporate high levels of alcohol and/or harsh surfactants into contemporary antimicrobial products, which have been shown to cause dryness and irritation to skin tissues.

While hundreds of different compounds registered with the EPA, claiming to effectively disinfect or sanitize against various microbes, the vast majority, if not all, of the registered compounds have one or more of the following undesirable characteristics: will leave a residue on the treated surface (which must be wiped away); are flammable (thus, considered a DOT hazard material subject to extra transport and storage restrictions and costs); are corrosive, to some degree, to the surfaces to which they are applied; are toxic to animals (human and non-human); and are, thus, not considered environmentally-friendly; a concept that has been coined in many industries, broadly, as being "Green."

In particular, the following undesirable characteristics have been identified with various currently-used chemical disinfectants: Ethanol and Isopropanol are slow in their germicidal action on surfaces, fairly ineffective against Gram positive bacteria and are not effective against spores. In addition, these are flammable compounds and require one to follow hazardous shipping requirements. Formaldehyde has a pungently irritating odor and is toxic. Phenols, which are basic to a number of popular disinfectants at high dilutions, are toxic, are flammable, and are not effective in ordinary usage against spores. Quartenary ammonium compounds often leave residues, are neutralized by anionic detergents, and are not tuberculocidal or sporicidal even at high concentrations. Hypochlorites are strong oxidizing agents and may function as disinfectants at the proper concentrations, but are, as a whole, corrosive to metals and can be dangerous to handle. Iodophors likewise may function as disinfectants at the proper concentrations, but leave stains (residue) and are often less effective if any appreciable amount of protein is present. Most heavy metal based antimicrobial agents are toxic and more bacteriostatic than bacteriocidal. Peroxides are widely used to clean skin surfaces and wounds, but they have negligible antimicrobial activity.

Microorganisms, including bacteria, fungi, algae, viruses, prions and other such microbial entities, can be found within any growth condition or environment where life exists. While many varieties of bacterial microbes are useful or 'friendly' to their animal-hosts, others prove irritating and troublesome—yet, relatively harmless—to manage their populations. Many strains of microbes pose a very serious—and often lethal—risk to the health of co-existent animal populations. Decreasing those troublesome, very serious, and lethal microbial populations under non-sterile conditions requires the use of an antimicrobial agent. Different bacteria show varying degrees of resistance toward a particular disinfectant. Prions tend to be the most-resistant of all microbial entities to antimicrobial agents. Bacterial spores and mycobacteria are generally considered to be the most resistant forms of the bacteria, followed by Gram-negative bacteria, which are generally considered to be more resistant than vegetative Gram-positive bacteria such as the staphylococci and enterococci.

Some aspects of the invention provide antimicrobial compositions and methods for using the same. In some embodiments, the antimicrobial compositions include an α-keto alkylperoxyacid. In other embodiments, the antimicrobial compositions include one or more of a peroxyacid, a hydroperoxide, a bis(hydroperoxide), or an epoxide. Surprisingly and unexpectedly, the present inventors have discovered that such compositions are also effective in disinfecting bacterial spores. Compositions of the invention can optionally include one or more additional antimicrobial agent (e.g., hydrogen peroxide), a pH neutral diluting solvent (e.g., water), or a combination thereof. Typically, the diluting solvent is a pH neutral liquid solvent adaptable for dissolving the α-keto alkylperoxyacid or other compounds of the present invention, e.g., water.

Other aspects of the composition can also include an additional agent that can attack the protective protein layer of microbes (for example, non-enveloped viruses or spores) and/or an additional agent that can dissolve the lipid nature of the envelopes or membranes of the microbes. Suitable additional antimicrobial agents include organic acids, peroxides, alcohols, and ethers.

In some embodiments, the concentration of α-keto alkylperoxyacid in solution is about 1,000 ppm or less, typically 500 ppm or less, often 400 ppm or less, more often 200 ppm or less, and most often 100 ppm or less. Yet in other embodiments, the composition comprises at least about 2.5% (v/v) of α-keto alkylperoxyacids.

As stated above, compositions of the invention can also comprise a second antimicrobial agent. In some cases, the amount of second antimicrobial agent can be at least 3% (v/v). Suitable second antimicrobial agents include those mentioned herein as well as other antimicrobial agents known to one skilled in the art. In one particular embodiment, the second antimicrobial agent is hydrogen peroxide.

Compositions of the invention can also include one or more of the additional agents. Exemplary additional agents include, but are not limited to, organic acids (such as dichloroacetic acid for protein disruption), other peroxides (for protein disruption), alcohols (such as diacetone alcohol for membrane disruption), and ethers (such as butylene glycol monomethyl ether for membrane disruption). Compositions of the invention have shown to be generally non-toxic and non-flammable. Compositions of the invention also evaporate relatively rapidly from a surface-of-interest leaving only an acceptable level of measurable residue.

In some embodiments of the invention, compositions of the invention are used to disinfect a gram-positive bacteria, a gram-negative bacteria, a bacterial spore, or a combination thereof. Unlike other conventionally known antimicrobial agents that are commercially used, compositions of the invention have been shown to be effective in not only disinfecting gram-positive bacteria, but also in gram-negative bacteria, and bacterial spores.

In many instances, compositions of the invention provide at least 6-log order complete kill or reduction of vegetative bacteria when applied to a surface. In other instances, compositions of the invention provide at least 5-log reduction of bacterial spores. Often, compositions of the invention provide a "complete kill" of the bacterial population atop the surface such that any functional bacteria remaining atop the surface-of-interest is/are not capable of re-populating to a measurable level, thereby rendering any toxicity or pathogenic functionality of the original bacterial population effectively null.

Compositions of the invention can be applied in aerosol form such as spraying from a bottle containing liquid antimicrobial agent onto a surface. Once applied to the surface, the composition is adapted to evaporate to dryness (to the touch), typically within about 10 to about 30 minutes while leaving acceptable levels if any) of measurable residue on the surface, such acceptable levels are generally set based on the surface on which the disinfectant is used. Compositions of the invention are typically non-flammable and of very low toxicity allowing them to be shipped as a non-hazardous chemical, per DOT guidelines. Moreover, solutions comprising the compositions of the invention often have low surface tension and are effective in the presence of proteins.

Compositions of the invention can be used to disinfect clean rooms, hospitals, veterinary and dental offices, laboratories (e.g., general medical/veterinary/dental, Q.A. manufacturing, new product development/R&D, and other laboratories), medical equipment and devices, household surfaces, sports equipment, as well as any suitable objects or surface so desired. Some of the characteristics of compositions of the invention include, but are not limited to, effectiveness at high dilutions in the presence of organic matter; a broad spectrum of antimicrobial activity-effectiveness against gram-positive, gram-negative bacteria, spores, viruses, and fungi); stable under the conditions of transport, storage and use; homogeneity; solubility in water, fats, and oils for good penetration into microorganisms; low surface tension for penetration into cracks and crevices; minimum toxicity-lack of acute and chronic toxicity, mutagenicity, carcinogenicity, etc.; capable of being applied with no residue after a desired period of time has passed; pleasant or minimal odor; non-flammable; low or no impact to plants and animals; and low cost.

Other aspects of the invention provide products that comprise the antimicrobial compositions of the present invention, as well as combinations of such products. Indeed, the combined and systematic use of products containing the antimicrobial compositions of the invention serves to eradicate microorganisms for a longer period of time and prevent their spread.

Some embodiments of the invention provide personal care products comprising the antimicrobial compositions disclosed herein. Suitable personal care products comprising the antimicrobial composition disclosed herein include, but are not limited to, hand soaps, hand sanitizers, body washes, mouth washes, toothpastes, shower gels, shampoos, body lotions, deodorants, nasal sprays, foot care, vaginal care and/or wash, pet care and combinations thereof.

In yet other aspects of the present invention, the personal care products disclosed herein take the form of a wipe product, particularly suitable for wiping or drying the face or hands. In such instance, the antimicrobial compositions of the invention are typically embedded or impregnated into the wipe product.

Still in other aspects of the present invention, the personal care product disclosed herein takes the form of a tissue or towel, also suitable for wiping or drying the face or hands. In another aspect of the present invention, the personal care product takes the form of a feminine napkin and/or a diaper. In another aspect of the present invention, the personal care product takes the form of a first aid antiseptic for irritated, injured, or acne-affected skin and/or for pre- or post-surgical use.

Yet other aspects of the invention provide antimicrobial compositions disclosed herein that are incorporated into one or more household care products. Indeed, suitable household care products for purposes of the invention include, but are not limited to, hard surface cleaners, deodorizers, fabric care compositions, fabric cleaning compositions, manual dish detergents, automatic dish detergents, floor care compositions, kitchen cleaners or disinfectants, bathroom cleaners or disinfectants and combinations thereof.

In other aspects of the invention, the household care product takes the form of a wipe or towel, suitable for household cleaning and/or care. In some embodiments of the invention, the household care products can comprise certain adjunct ingredients. Exemplary adjuncts include, but are not limited to, detersive enzymes, builders, bleaching agents, bleach activators, transitional metal bleach catalysts, oxygen transfer agents and precursors, soil release agents, clay soil removal and/or anti-redeposition agents, polymeric dispersing agents, brightener, polymeric dye transfer inhibiting agents, chelating agents, anti-foam agents, alkoxylated polycarboxylates, fabric softeners, perfumes, carriers, hydrotropes, processing aids, dyes or pigments, solvents for liquid formulations, solid fillers, detersive surfactants and combinations thereof.

Yet still in other aspects of the invention, the antimicrobial compositions disclosed herein can be incorporated into a skin care product. In such aspects of the invention, the skin care product incorporates a dermatologically acceptable carrier to facilitate safe transfer of the antimicrobial composition disclosed herein to the desired area of the skin. In some embodiments, the skin care product can include certain adjunct ingredients. Suitable adjuncts include, but are not limited to, other antimicrobial and antifungal actives, surfactants, desquamation actives, anti-acne actives, anti-wrinkle actives, anti-atrophy actives, anti-oxidants, radical scavengers, chelators, flavonoids, anti-inflammatory agents, anti-cellulite agents, topical anesthetics, tanning actives, sunscreen actives, conditioning agents, thickening agents, detackifying agents, odor control agents, skin sensates, antiperspirants and mixtures thereof. Other suitable adjunct ingredients are well known to one skilled in the art. See, for example, U.S. Pat. No. 6,294,186, which is incorporated herein by reference in its entirety.

It is particularly desirable that an antimicrobial containing one or more of a peroxyacid, a hydroperoxide, a bis(hydroperoxide), or an epoxide be available for use as a single, stable gel or a viscous solution (sol), although a solid would be satisfactory if it were biodegradable, easily soluble in water, and did not contain significant inorganic dissolved solids such as are provided by sodium persulfate or sodium perborate. It is also desirable for the antimicrobial to have less odor, be non-corrosive and promote wound healing.

The embodiments disclosed herein overcome the problems of the prior art by providing an aqueous composition comprising stable sols, gels and solids one or more of a peroxyacid, a hydroperoxide, a bis(hydroperoxide), or an epoxide. In some embodiments, the aqueous composition comprises stable sols, gels and solids comprising a peroxy acid and a bis(hydroperoxide). In some embodiments, the peroxyacid is a C2 to C6 peroxycarboxylic acids. In other embodiments, the compositions of the invention provide a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the peroxycarboxylic acid is peracetic acid (C2) peroxy propionic acid (C3) peroxybutanoic acid (C4), peroxysuccinic and peroxymalonic acid. Such compositions form carriers for delivering peroxycarboxylic acids for applications related to high level disinfectants/sterilants of vegetative bacteria, spores and biofilms.

The compositions are particularly useful for killing vegetative bacteria and spores at the level acceptable to be called disinfectants. Unlike most peroxy carboxylic compounds, it was discovered that the non a-keto peroxyacid compounds in combination with keto peroxyacids do not require an acid catalyst for efficient synthesis and are effective against biofilms. Without the need for a toxic catalyst for synthesis, the mixture of the embodiments disclosed herein typically contains water, hydrogen peroxide, a peroxyacid, a hydroperoxide, a bis(hydroperoxide), and an epoxide, all of which work synergistically and are beneficial to healing of a wound.

Many of the parent compounds (i.e., the corresponding carboxylic acids) of the embodiments disclosed herein are present within nearly all living cells and play significant roles in essential cellular metabolism. For example, the parent carboxylic acid compounds of peroxypyruvic acid, peroxy oxaloacetate, peroxy a-keto glutarate, are key compounds within the TCA cycle, the predominant energy producer for cellular metabolism. The parent compound of peroxy alpha keto butyric acid, i.e., alpha keto butyric acid, is involved in the metabolic production of succinyl-CoA which is also used in the TCA cycle and thus contributes to cellular energy production. Alpha keto valeric acid, the parent compound of peroxy alpha keto valeric acid, is an intermediate in protein synthesis and the biosynthesis of the amino acids such as leucine and valine. Alpha keto valeric acid is involved in gluconeogenesis in cells. Pyruvate is involved in producing energy for hypoxic cells during wound healing through glycolysis. The potential harmful effects of the ROS can be mediated by a-keto acids. In addition, pyruvate is involved in protecting DNA during hypoxia and is an indirect metabolic contributor to collagen deposition and angiogenesis in wound healing. Moreover, pyruvic acid accelerates the debridement of the dead skin in both wounds and burns.

Studies show that many widely used wound antiseptics have undesired cytotoxicity, and while some do kill bacteria at a sufficient level, they often do not promote a relatively fast wound healing. In many cases, irrigation of open fracture wounds with an antibiotic solution offers no significant advantages over the use of a nonsterile soap solution and may in fact increase wound-healing problems.

To be useful, topical antiseptics should be toxic to bacteria but should have no significant toxicity to underlying tissues, and ideally, they should also preserve or enhance host defense against infection. The present invention provides a method for treating wounds including, but not limited to, surgical, traumatic, chronic and burn wounds. Methods of the invention promote wound healing and typically rapidly kill high levels of viruses, vegetative bacteria, fungi, mycobacteria and spores. Unlike many conventional antiseptics available today, compositions and methods of the invention eliminate bacteria, enhance body's defense system, and enhance the healing process. Without being bound by any theory, it is believed that these benefits are achieved at least in part by the synergistic effect of the parent a-keto acids working together with resultant alpha-keto peracid and a non-alpha keto peroxyacid. It is believed that the synergetic effect results in energy generation and serves as intermediates in the generation of other biomolecules that are useful in wound healing.

In addition, the combination of the peracids and bis (hydroperoxides) disclosed in the present embodiments can kill high levels of bacteria and spores in biofilms and in high protein environments without being corrosive and having virtually no cellular toxicity issues.

It should be appreciated that because the stability of peracids and bis(hydroperoxides) are often limited, in many instances compositions of the invention can include the presence of the parent carboxylic acid. As used herein, the term "parent carboxylic acid" refers to the corresponding carboxylic acid in which the peracid is derived from or is degraded into under a typical storage or production conditions. In some embodiments, the parent carboxylic acid is present in the composition of the invention in an amount of about 120.4 mM or less, typically, about 12.4 mM or less, more typically, about 6.2 mM or less, often about 2.5 mM or less, more often, about 1.2 mM or less, still more often about 0.62 mM or less, yet more often about 0.31 mM or less, and most often about 0.062 mM or less.

Still in other embodiments, compositions of the invention can include hydrogen peroxide. Typically, the amount of hydrogen peroxide present in the wound healing compositions of the invention is about 715 mM or less, typically about 71.5 mM or less, more typically about 35.8 mM or less, often about 14.3 mM or less, more often about 7.2 mM or less, still more often about 3.6 mM or less, yet more often about 1.8 mM or less, and most often about 0.35 mM or less.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

Example 1

This example illustrates one method of testing the antimicrobial effects of compounds of the invention.

Kill Time Test

This is a test performed to demonstrate log reduction values over time for a disinfectant against selected bacteria, fungi, and/or mold. A representative list of the organisms tested include, but are not limited to, *Bacillus subtilis, Bacillus atrophaeus, Bacillus thuringiensis, Staphylococcus aureus, Salmonella cholerasuis, Pseudomonas aeruginosa, Aspergillus niger*, and *Trichophyton mentagrophytes*. The following exemplifies one procedure derived from disinfectant test methods found in guidelines of the Association of Official Analytical Chemists (AOAC) to meet "log reduction criteria" established by the U.S. Environmental Protection Agency (EPA) and U.S. FDA for certain applications: (1) A tube of the sample-disinfectant is placed into a waterbath for temperature control and allowed to equilibrate; (2) Once the tube has reached temperature, it is inoculated to achieve a concentration of approximately $10^6$ CFU/mL; (3) At selected time points (generally five points are used including zero) aliquots are removed and placed into a neutralizer blank; (4) Dilutions of the neutralizer are made and selected dilutions plated onto agar; (5) Colonies are enumerated and log reductions are calculated.

Preparation of Bacterial Suspensions

In order to obtain observable significant reductions (on the order of $10_6$) of surface bacteria, a high number of viable CFU/in$^2$ must be available for treatment on the surface to be disinfected. Since a substantial number of organisms die during the drying process, it is necessary to start with bacterial suspensions that exceed the concentration desired on the final surface. It has been found that a suspension prepared from an agar plate that has been stored refrigerated over-night yields a relatively even surface film upon application and drying. The cool overnight storage of the agar plate reduces the surface tension of the subsequent suspension. Suspensions were prepared in sterile skim milk medium (SM) by harvesting the organism from the agar plate using a sterile cotton swab and vigorously vortex mixing to achieve homogeneity. A viable concentration of $10^8$-$10^9$ CFU/mL was used. Most non-fastidious organism suspensions can be retained in the cooler for several days, and were used as long as enumeration demonstrated satisfactory viability.

Test Surface Preparation

Glass cover slips (e.g., 25 mm$^2$) were used as the test surface for this procedure. Sterile slides were used for this procedure. Slides were sterilized by placing them in layers separated by filter paper (e.g., Whatman #1) and placing them in an aluminum envelope then baking at 150-170° C. for 1-2 hours.

The microorganism film was prepared by dispensing 20 μL of suspension onto a sterile slide and spreading the suspension drop over the surface of the slide. A sterile inoculating needle that has been bent in the shape of a hockey stick was used. The slide were placed on the pins of a sterile disposable plastic 96 well inoculating head that had small drops of sterile water placed onto some of the pins to help hold the slide in place during preparation. The suspension was spread as near to the edges of the slide as possible without touching the edge. The drop was respread once more when necessary without over spreading. The suspension was allowed to dry uncovered at room temperature. Inoculated slides were used as soon as possible, often the same day to minimize loss of viability.

Disinfectant Application

Care was taken during treatment application to assure consistency between slides and experiments. Disinfectants were applied to inoculated slides with an air brush (e.g., Iwata revolution R4500) from a distance of 20-30 cm and a 12-18 psi setting of the compressor output regulator. Travel time for a treatment pass was about 1 ft/sec. Methods were adjusted in order to maintain consistent application between slides. Slides were air dried uncovered at room temperature.

Enumeration

The effectiveness of treatments was evaluated by enumeration of the surviving bacteria on the slide. The bacteria were removed from the slide and the disinfectant was neutralized by immersion of the slide in Letheen broth (LB). The bacteria were then plated in appropriate dilutions. A positive control was included for comparison to assess efficacy.

To enumerate viable organisms on a slide, the slide was placed into a 50 mL centrifuge tube containing 20 mL of LB. The tube was vigorously shaken for 5 seconds and then vortexed for 5 seconds. Mixing step was repeated once. The LB was diluted in peptone, and was plated on an appropriate agar to attain countable dilutions. The LB tube (for decreased limit of quantitation) and agar plates were incubated overnight at the appropriate atmosphere and temperature.

Typically, for an effective disinfectant, about 50 μL of the LB tube was logarithmically spiral plated (DF=20) onto the appropriate agar. In some cases, LB was plated at higher dilutions, e.g., transferred 90 μL of LB to 9 mL of peptone and spiral plated 50 μL (DF=2000).

The CFU/slide was calculated using the spiral plater counting tables and multiplying by the dilution factor. Viability loss due to disinfection was determined by comparing treated slide values with the untreated positive control.

Example 2

Various concentrations of peroxy pyruvic acid generated from different compositions of a mixture from pyruvate, hydrogen peroxide ($H_2O_2$), and water were tested to determine the log reduction of Bacillus cereus spores. These spores had been incubated for 7 years and thus the possibility of vegetative cells remaining was very low. Each sample of dilute pyruvate and hydrogen peroxide solution noted in Table 2 was tested employing the spray test outlined above. Slides of MRSA were treated with peroxy pyruvic acid derived from the composition of 10% pyruvate and 3% $H_2O_2$ as a control. The log reduction of the MRSA control was approximately 6-logs, there was no growth in the broth used to plate for enumeration, therefore, it was assumed that complete elimination of the MRSA population was accomplished. As in Example 1 above, the water used in these studies is USP purified.

TABLE 1

Log Reduction of *Bacillus cereus* spores
Positive *B. cereus* Control (BC 2) log = 5.7
Positive MRSA Control (Sta 25) log = 8.3

| Solution No. | Organism | % $H_2O_2$ | % Pyruvate | Log Reduction |
|---|---|---|---|---|
| 2 | MRSA | 3 | 10 | >5.7* |
| 1 | BC 2 | 1 | 10 | 1.1 |
| 2 | BC 2 | 3 | 10 | >3.5 |
| 3 | BC 2 | 1 | 5 | 0.4 |
| 4 | BC 2 | 3 | 5 | 5.7* |
| 5 | BC 2 | — | 10 | 1.1 |
| 6 | BC 2 | — | 5 | 0.8 |

*Total kill/destruction of microbes, i.e. no growth in Letheen broth tubes (3 reps).

Example 3

Peroxy pyruvic acid was synthesized as follows. Pyruvic acid was added to hydrogen peroxide at a temperature of between −30° C. and 10° C. until a conglomerate layer formed on the bottom of the flask. The reaction was allowed to stand without stirring until all pyruvic acid had dissolved into solution. Formation of peroxy pyruvic acid was confirmed by mass spectrometer and by chemical reaction.

Example 4

The reaction of Example 3 was repeated with the addition of Sulfuric Acid ($H_2SO_4$) as a catalyst. An ice bath was used to keep the reaction cool resulting in quantifiable amounts of perpyruvic acid production.

Example 5

Reaction of Examples 3 and 4 were repeated for α-Ketobutanoic Acid ($CH_3CH_2COCOOH$) and α-Ketovaleric Acid ($CH_3CH_2CH_2COCOOH$) to produce the corresponding α-keto peracids.

Example 6

FIG. 1 shows efficacy of peroxy pyruvic acid against *C. difficile* using sulfuric acid catalysts and methods of Example 1 above. All efficacy studies for *C. difficile* were done according to the Official Method 966.04 "Sporicidal Activity of Disinfectants."

Figure 2:
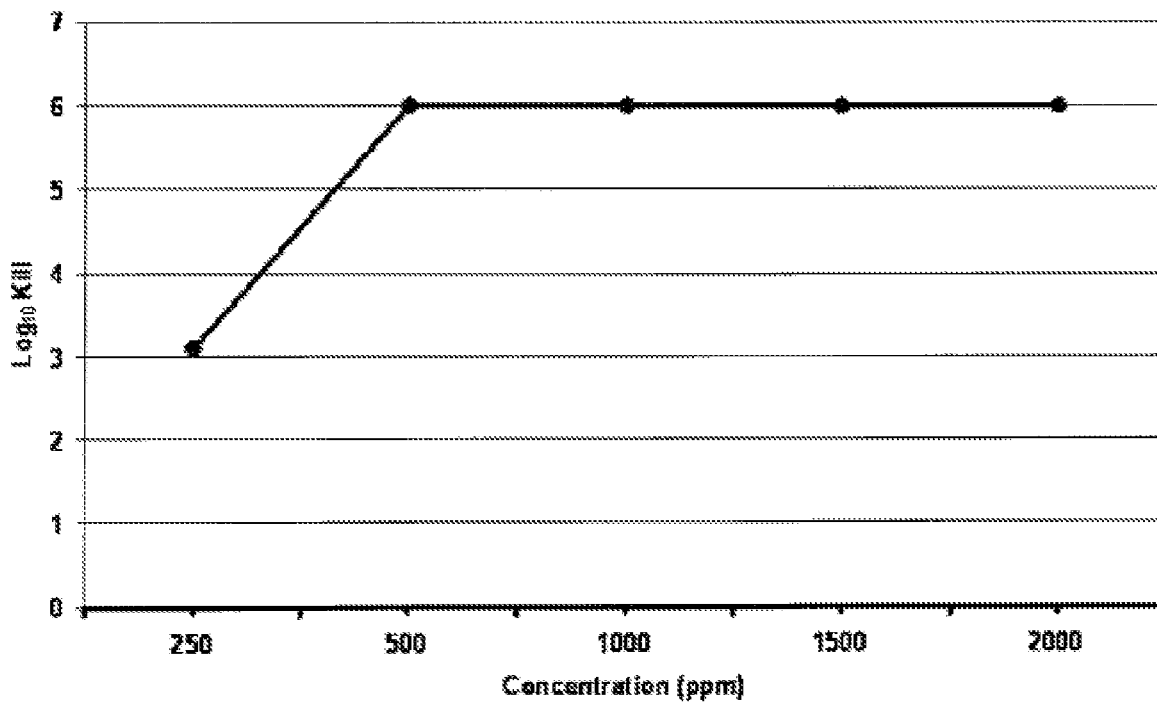
FIG. 2 is a graph showing efficacy of peroxy α-keto butyric acid against *C. difficile* at various concentrations.
Figure 5:
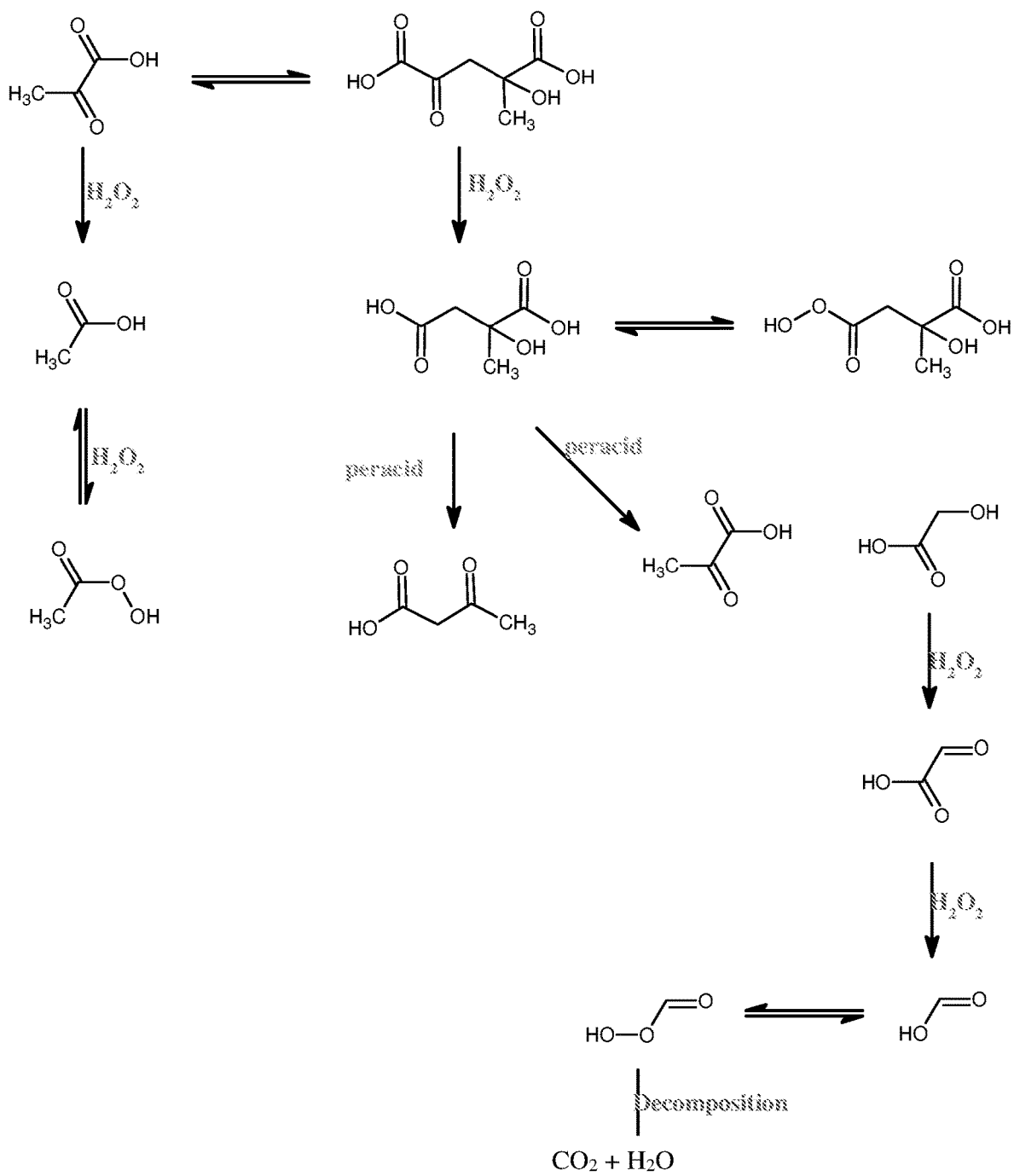
FIG. 5 is a reaction scheme for a reaction comprising pyruvic acid and hydrogen peroxide according to an embodiment of the present invention.
Figure 6:
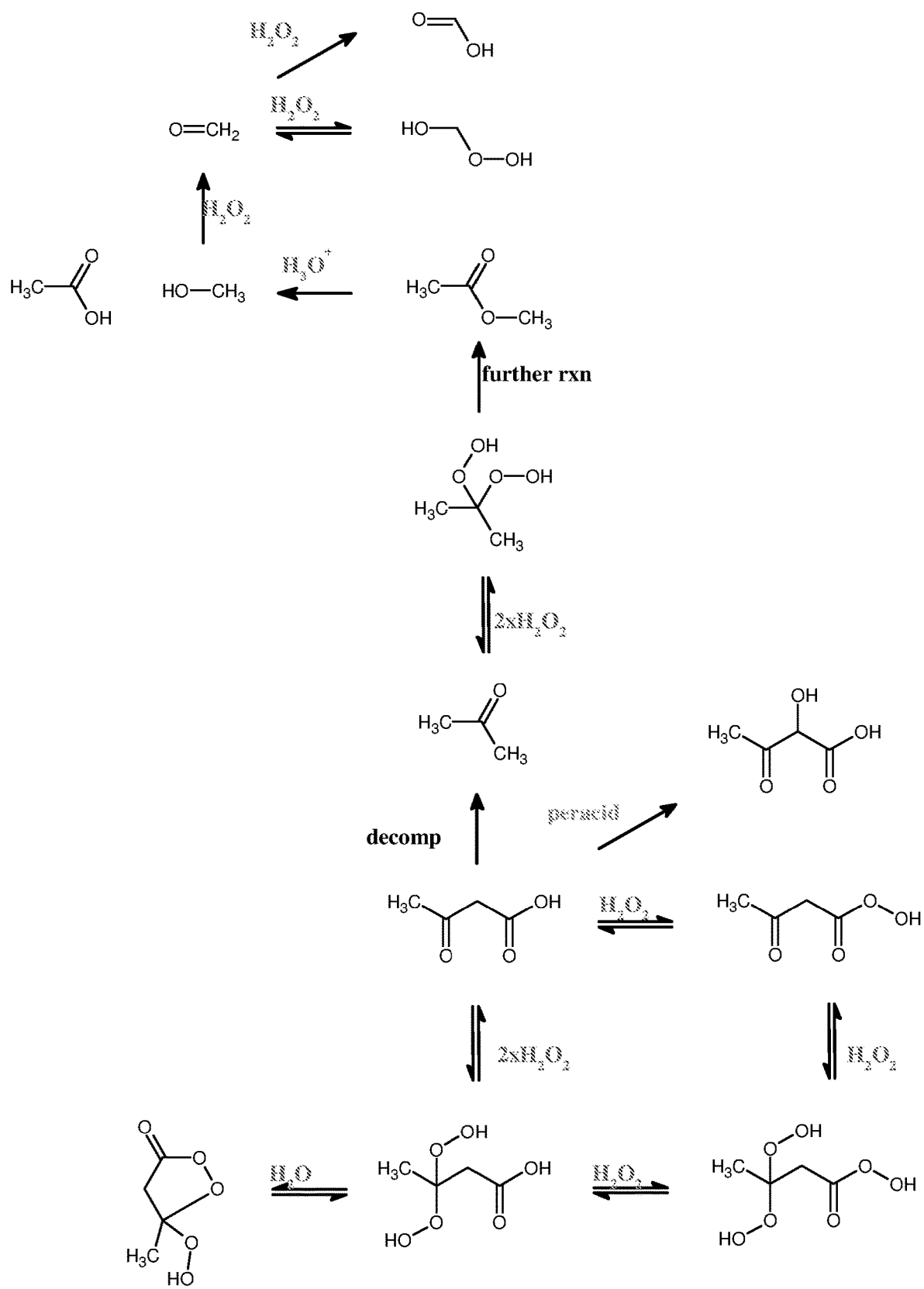
FIG. 6 is a reaction scheme for a reaction comprising acetoacetic acid and hydrogen peroxide according to an embodiment of the present invention.
Figure 7:
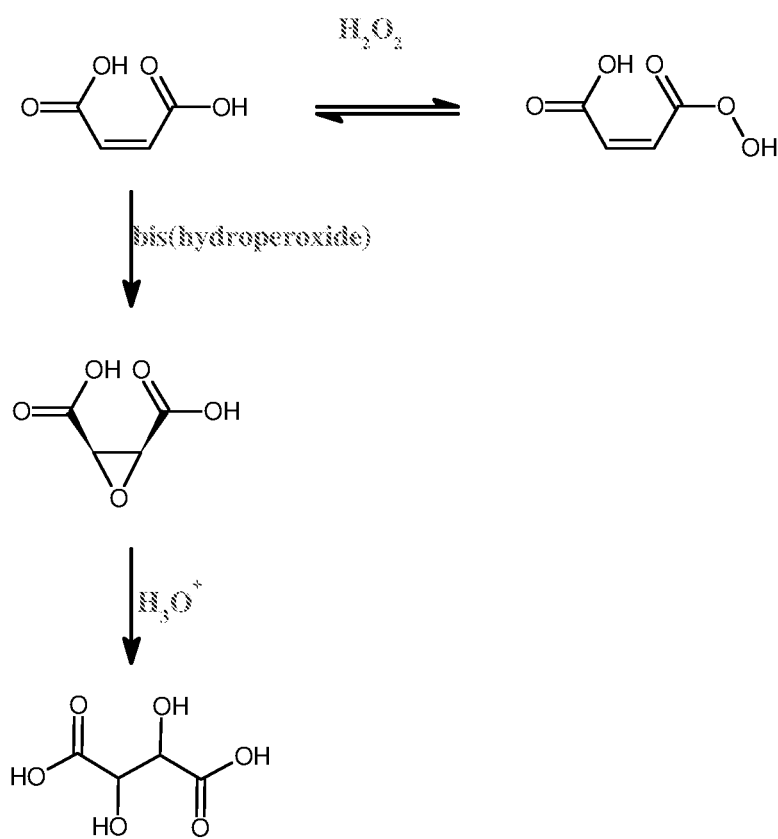
FIG. 7 is a reaction scheme for a reaction comprising maleic acid and hydrogen peroxide according to an embodiment of the present invention.
Figure 8:
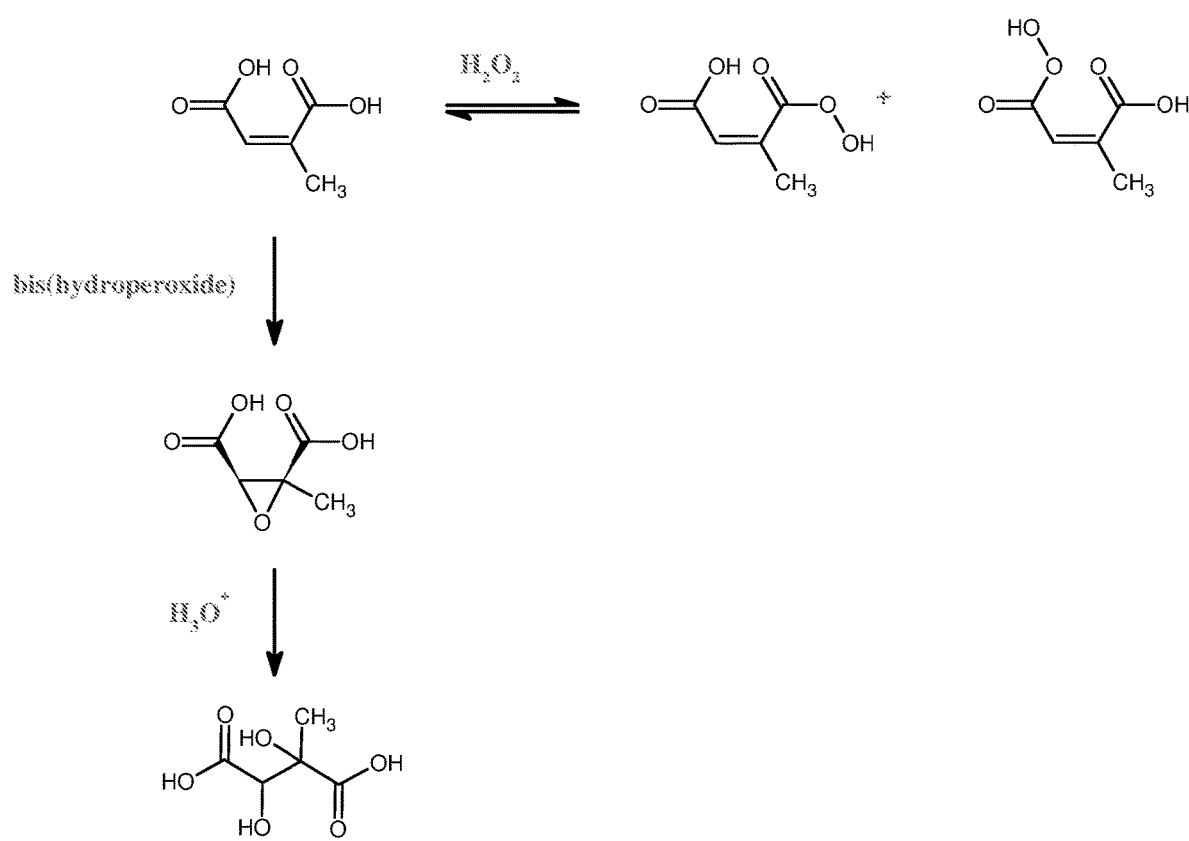
FIG. 8 is a reaction scheme for a reaction comprising citraconic acid and hydrogen peroxide according to an embodiment of the present invention.

FIG. 2 shows efficacy of peroxy alpha keto butyric acid against *C. difficile*.

Example 7

In another experiment, 15 ml of 30% Hydrogen Peroxide was stirred using a stir bar while adding 0.25 ml of the Pyruvic acid in increments every 1.5 minutes. In one instances, the reaction was carried out at room temperature and in another instances at 5° C. Titration of the resulting mixtures showed that there was no observable peracid formation.

Example 8

When preparing Peroxy-alpha-Ketobutyric Acid (POKBA) from alpha-Ketobutyric Acid, some modifications were needed due to the physical nature of the material. Alpha-Ketobutyric Acid is a hygroscopic solid that melts at 30-34° C. Thus, it is often present as a mixture of liquid and solid. The liquid was added first and this initiated the reaction after approximately 10% of the total weight had been added. This was a marked departure from the preparation of peroxypyruvic acid, in which the reaction initiates almost immediately with the first addition of the pyruvic acid.

As in the preparation of perpyruvic acid, the hydrogen peroxide was held at about 4° C. When the last of the liquid alpha-Ketobutyric Acid had been added, it becomes necessary to either add a solid or to add a liquid (obtained by immersing the container with the acid into a hot water bath at 50° C. The resultant melt was then added in the same manner as before except that, since a warm liquid was being added to a cold liquid, the additions were made with greater time periods between them so as to allow the temperature to re-equilibrate. In addition, upon contact with the cold liquid some of the melted solid froze, thus causing a small amount of solid to sink to the bottom. This solid reacted and the greater time periods between additions became necessary.

Overall, it is believed that this reaction proceeded somewhat slower than the perpyruvic acid synthesis, although it was essentially complete within a week as in the case with Pyruvic acid when prepared without a catalyst.

Example 9

Pyruvic peracid (PPA) and Peroxy α-ketobutyric acid (POKBA) were tested against *C. difficile* using the ASTM E2197-02 testing method and the results are shown on FIG. 3. As the graph shows, POKBA is significantly more active compared to PPA. The method of testing these molecules against *C. difficile* was designed to evaluate the ability of liquid chemical germicides to inactivate vegetative bacteria, viruses, fungi, mycobacteria and bacterial spores in the presence of a soil load on disk carriers that represent environmental surfaces and medical devices. It was also designed to have survivors that can be compared to a mean of no less than three control carriers to determine if the performance standard has been met: The test protocol did not include any wiping or rubbing action.

This test method is a standard test promulgated by ASTM Committee E35 on Pesticides and Subcommittee E35.15 on Antimicrobial Agents. The stringency in the test is provided by the use of a soil load, the microtopography of the carrier surface and the small ratio of disinfectant to surface area (1:5) typical for many disinfectant applications. Thus the formulation under test is presented with a reasonable challenge while allowing for efficient recovery of the test organisms from the inoculated carriers with or without their exposure to the test formulation.

The metal disks used in the basic test are also compatible with a wide variety of germicidal actives and most surfaces in consumer based product manufacturing and health care facilities. The design of the metal discs makes it possible to place onto each precisely measured volume of the test organism (28 µL) as well as the test formulation (125 µL). The inoculum is placed at the center of each disk whereas the volume of the test formulation covers nearly the entire disk surface thus eliminating the risk of any organisms remaining unexposed to the test formulation. The relatively small ratio of 1:5 between the volume of the inoculum and that of the test formulation closely reflects many field applications of liquid chemical germicides. In all tests other than those against viruses, the addition of 9.95 mL of a diluent gives a 1:200 dilution of the test formulation immediately at the end of the contact time. While this step in itself may be sufficient to arrest the germicidal activity of most formulations, a Letheen Broth (LB) was used as a specific neutralizer and diluent.

The soil load used in this test was a mixture of three types of proteins (high molecular weight proteins, low molecular weight peptides and mucous material) and consisted of a mixture of 0.5 g of tryptone, 0.5 g of BSA, and 0.04 g of bovine mucin in 10 mL phosphate buffer (pH 7.2). These solutions were prepared separately and sterilized by passage through a 0.22 µm pore diameter membrane filter, aliquoted and stored at either 4° C. or −20° C. To obtain 500 µL of the inoculum for the discs, 340 µL of the microbial suspension was added to 25 µL of BSA, 100 µL of mucin, and 35 µL of tryptone stock.

Stainless Steel Disks (1 cm in Diameter and Approx. 0.7 mm Thick) were prepared from sheets of magnetized and brushed stainless steel 10 similar to that used in the manufacture of countertops. The disks were soaked in a detergent solution for at least one hour to degrease them and then washed and sterilized by autoclaving.

*C. difficile* was prepared by suspending a *C. difficile* suspension overnight into pre-reduced Brain heart infusion broth (BHI) and allowed to grow overnight. Inoculates from the BHI were streaked onto the surface of a sufficient number of pre-reduced trypticase soy agar plates with 5% sheep blood (BA) for confluent growth using a swab wetted in the prepared suspension (i.e., containing 1 mL of spore suspension). The BA plates were incubated for 14-28 days anaerobically. Afterwards, the cells were harvested from the agar by adding 3 mL of sterile distilled water to the surface of the BA plate and suspended using a bent glass rod to suspend the cells from the plate into the water. A combined rinsing of each plate was added into one or more 50 mL centrifuge tube(s). The cells were centrifuged at 4500 rcf for 15 minutes and the supernatant carefully discarded. These steps were repeated two additional times. The final 10 mL of spore suspension was heated in a 65-70° C. water bath (assuring the entire tube is immersed) for 30 minutes. The final concentration of spores in the suspension were checked for the purity of the spores by preparing a 1:1000 dilution in anaerobic broth and spiral plating 50 µL onto reduced BA plates. The spores were stored at 2-8° C. until needed.

The disks were inoculated with 25 µl, of $10^6$ C. difficile spores suspended in the soil load and allowed to dry. Afterwards, 125 µL of different concentrations of the alpha Keto peroxy acids (AKPA) were added to the discs and allowed to set for 10 minutes before dilution into the LB neutralizer. Afterwards, the LB neutralizer was vortexed for 5 seconds and 50 µL of the LB in the tube was logarithmically spiral plated (DF=20) onto the appropriate agar. Controls were treated similarly as with the AKPA with the exception that water replaced the AKPA.

Example 10

Various carboxylic acids and peroxy α-keto carboxylic acids were tested against various microorganisms. The results are shown in FIG. 4. A series of methods were used for testing the microbes and are defined by the column titles on the Table in FIG. 4. The details of these methods are as follows.

Preparation of Bacterial Suspensions

In order to obtain observable significant reductions (on the order of $10^6$) of surface bacteria, a high number of viable $CFU/in^2$ must be available for treatment on the surface to be disinfected. Since a substantial number of organisms die during the drying process, it is necessary to start with bacterial suspensions that exceed the concentration desired on the final surface. It has been found that a suspension prepared from an agar plate that has been stored refrigerated overnight yields a relatively even surface film upon application and drying. The cool overnight storage of the agar plate reduces the surface tension of the subsequent suspension. Suspensions were prepared in sterile skim milk medium (SM) by harvesting the organism from the agar plate using a sterile cotton swab and vigorously vortex mixing to achieve homogeneity. A viable concentration of $10^8$-$10^9$ CFU/mL is typically used. Most non-fastidious organism suspensions can be retained in the cooler for several days, and used as long as enumeration demonstrates satisfactory viability. Spore suspensions can be used directly or diluted to achieve the desired concentration of organism.

Test Surface Preparation

Sterile glass cover slips (e.g., 25 $mm^2$) were used as the test surface for the spray test and the immersion test. Slides were Sterilized by placing them in layers separated by filter paper (e.g., Whatman #1) and then in an aluminum envelope and baking them at 150-170° C. for 1-2 hours.

The organism film on the slide was prepared by dispensing 20 µL of suspension onto a sterile slide and spreading the suspension drop over the surface of the slide. With a sterile inoculating needle that has been bent in the shape of a hockey stick. Sometimes it is helpful to rest the slide on the pins of a sterile disposable plastic 96 well inoculating head that has had small drops of sterile water placed onto some of the pins to help hold the slide in place during preparation. The suspension was spread as near to the edges of the slide as possible without touching the edge. Care was taken to not allow organisms onto the reverse side of the slide, as it will not be exposed to disinfectant when treated. The suspension was allowed to dry uncovered at room temperature. The Inoculated slides were used the same day as prepared to minimize loss of viability.

Spray Test

Disinfectants were applied to inoculated glass coverslips with an air brush (e.g., Iwata revolution R4500) from a distance of 20-30 cm and a 12-18 psi setting of the compressor output regulator. Travel time for a treatment pass was ~1 ft/second. Treated slides were air dried uncovered at room temperature.

Immersion Test

Organisms were prepared on slides as indicated above. The carrier slides with the organisms were placed in 20±2 mL of disinfectant and allow to soak for the desired amount of time. After 10 minutes, the carrier slides were placed into LB broth and enumerate discussed below.

Organism Enumeration

The effectiveness of treatments was evaluated by enumeration of the surviving bacteria on the slide versus positive controls which had been treated with water. The positive controls demonstrated how many surviving bacteria were on the carrier slides when not treated with disinfectant. The bacteria are neutralized and removed from the slides by vortexing them in Letheen broth (LB) and then plating for counts by pipetting 50 µL of the appropriate dilutions in the LB tubes onto a plate and logarithmically spiral plating (DF) onto the appropriate agar. Also, direct dilution of the original suspension was directly enumerated to determine if there was any viability loss in the organism suspension due to desiccation.

AOAC 966.04 Test Against B. subtilis

This test is applicable to testing germicides for presence or absence of sporicidal activity against specified spore forming bacteria in various situations and potential efficacy as sterilizing agent. The organism typically used for testing disinfectants for use against bacteria and bacterial spores with medical devices such as endoscopes, catheters, and etc. is B. subtilis spores because they are known to form biofilms which are difficult to eradicate. This is done by testing the disinfectants for sporicidal kill of the spores which are attached to ceramic penny cylinders.

The B. subtilis spores were formed by inoculating nutrient agar (NA) slants and then washing growth on the slants with 10 mL of sterile deionized water and transferring to Roux bottles containing antibiotic medium #2 (AM #2) with $MnSO_4$. The bottles were placed in a water bath at 65-70° C. water bath for 30 min. Afterwards the spore suspension was centrifuged at ~4500 rpm for 15 min. The supernatant was decanted and the spores resuspended with ~20 mL of sterile water. The centrifugation and resuspension of the spores was repeated 3× more with intermittent homogenization. Finally the B. subtilis spore pellet was placed in a 65-70° C. water bath for 30 min then resuspended in 30 mL of sterile water. Afterwards, the suspension was streaked onto nutrient agar for determination of purity.

Evaluation of disinfectants against B. subtilis was done by attaching the spores to Porcelain cylinders, 8±1 mm od, 6±1 mm id, 10±1 mm long which had been sterilize by incubation for 2 h in 180° C. air oven. Afterwards the penny cylinders were washed with Triton X-100 and rinsed with water 4 times. The contaminated spores were gently placed into the disinfectant in test tubes for 10 minutes and then removed and placed into 10 mL±0.1 mL of LB neutralizer.

The neutralizer tubes were sonicated for 5±1 minute in a room temperature water bath. Afterwards, the tube containing penny cylinders were vortexed and diluted for enumeration by the above described method. Positive controls were penny cylinders that had only been exposed to sterile water.

Example 11

In another experiment, 5 mL of 30% hydrogen peroxide at 0-1° C. was stirred using a magnetic stir bar. 84-μL aliquots of pyruvic acid were added approximately every 90 s for 19 aliquots (totaling 27 min). During addition of the pyruvic acid and in the time spent stirring afterwards, temperature of the ice bath was measured in the 0-6° C. range. After the final pyruvic acid addition, the product sat in the bath slowly warming to room temperature. 98 min after the last pyruvic acid addition, stirring was terminated.

Figure 9A:
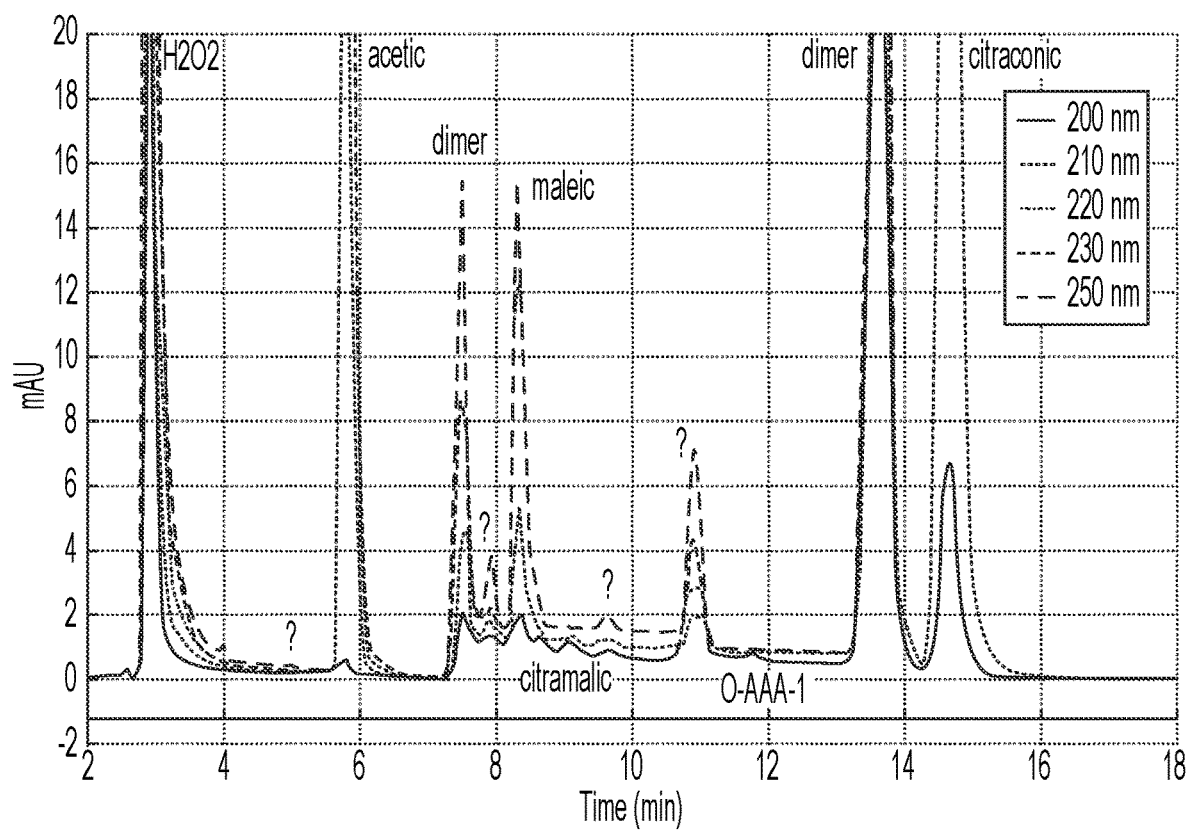
FIG. 9A shows HPLC analysis of pyruvic acid-hydrogen peroxide reaction after 2.4 hr using a 1:24 v/v dilution. The small peak at 4.0 min is likely the remaining unreacted pyruvic acid.

The reaction products were measured by HPLC analysis several times during the first 40 days after the reaction. The first measurement was performed just 2.4 hr after the final pyruvic acid addition. This chromatogram is shown in FIG. 9A.

Figure 9B:
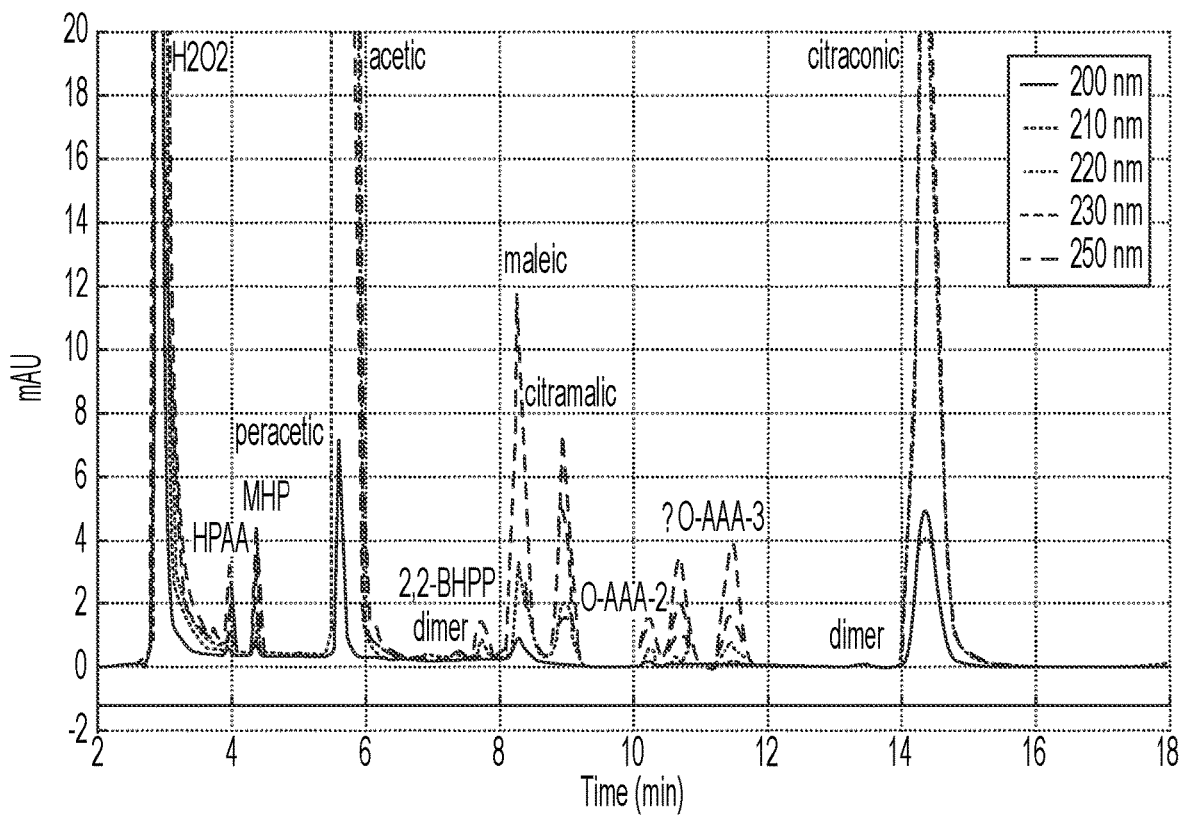
FIG. 9B shows HPLC analysis of pyruvic acid-hydrogen peroxide reaction after 5 days using a 1:24 v/v dilution. Only the most prominent peaks are labeled for clarity.

FIG. 9B was collected when the reaction was only 5 days old. After 5 days, the majority of the two dimer species have reacted. That citramalic acid is their primary product is evident by the large increase in its peak. Peracetic acid is also a major component at this point. Significant amounts of the oxidized acetoacetic acid species and the main product of their hydrolysis, 2,2-bis(hydroperoxy)propane, are also present.

Figure 9C:
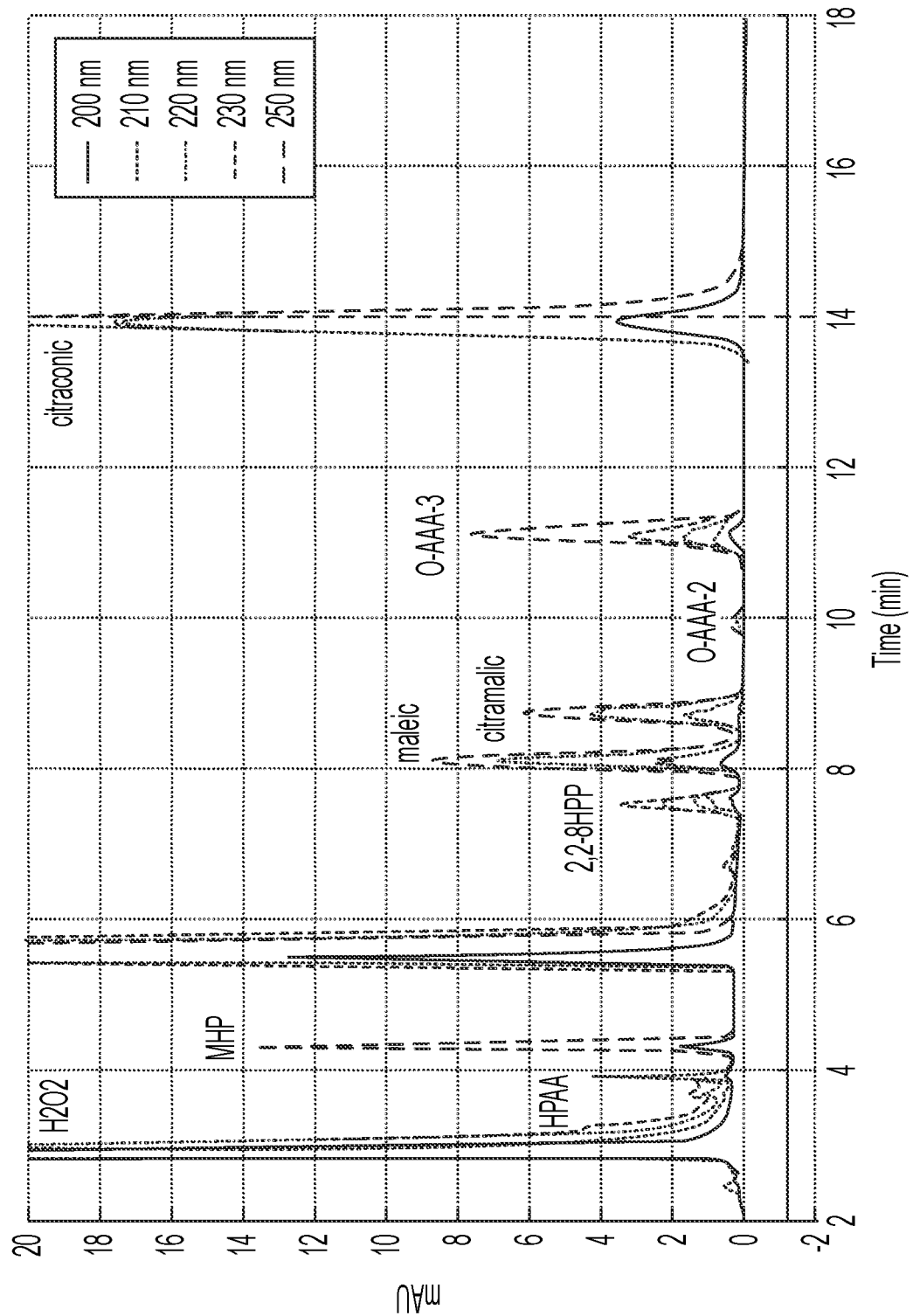
FIG. 9C shows HPLC analysis of pyruvic acid-hydrogen peroxide reaction after 40 days using a 1:24 v/v dilution. Only the most prominent peaks are labeled for clarity.

The 40-day-old reaction analysis is shown in FIG. 9C. The presence/absence of each individual component directly detectable by HPLC is shown in Table 2.

TABLE 2

| Compound | This Work (at 40 Days) |
|---|---|
| Hydrogen Peroxide ($H_2O_2$) | ✓ |
| Nitrate | |
| Hydroxymethyl Hydroperoxide (HMHP) | ✓ |
| Tartaric Acid | x |
| Formic Acid | ✓ |
| Performic Acid | ✓ |
| cis-Epoxysuccinic Acid | |
| Hydroperoxyacetic acid (HPAA) | ✓ |
| Methyl Hydroperoxide (MHP) | ✓ |
| Methyltartaric Acid | ✓ |
| Peracetic Acid | ✓ |
| Acetic Acid | ✓ |
| Permaleic Acid | ✓ |
| cis-Epoxymethylsuccinic Acid | ✓ |

TABLE 2-continued

| Compound | This Work (at 40 Days) |
|---|---|
| Oxidized Acetoacetic Acid-1 (O-AAA-1) | ✓ |
| 2,2-Bis(hydroperoxy)propane (2,2-HBPP) | ✓ |
| Unknown 1 (~7.65 min) | ✓ |
| Maleic Acid | ✓ |
| Citramalic Acid | ✓ |
| Oxidized Acetoacetic Acid-2 (O-AAA-2) | ✓ |
| Fumaric Acid | |
| Oxidized Acetoacetic Acid-3 (O-AAA-3) | ✓ |
| Citraconic Acid | ✓ |
| Unknown 2 (~16.3 min) | x |
| Mesaconic Acid | ✓ |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for healing a wound in a subject comprising contacting the wound with a therapeutically effective amount of a composition comprising acetoacetic acid, or a salt of acetoacetic acid, wherein the composition further comprises a hydroperoxide.

2. The method of claim 1, wherein salt of acetoacetic acid is a lithium, sodium, potassium, rubidium, cesium, magnesium, or calcium salt.

3. The method of claim 1, wherein the composition further comprises a keto acid.

4. The method of claim 1, wherein the composition further comprises pyruvic acid, parapyruvic acid, or citramalic acid, any of their salts, or mixtures thereof.

5. The method of claim 1, wherein the composition further comprises an acetoacetate ester.

6. The method of claim 1, wherein the composition further comprises hydrogen peroxide.

* * * * *